(12) United States Patent
Evers et al.

(10) Patent No.: US 10,942,178 B2
(45) Date of Patent: Mar. 9, 2021

(54) LONG RIGID SPACERS TO ENHANCE BINDING KINETICS IN IMMUNOASSAYS

(71) Applicant: KONINKLIJKE PHILIPS N.V., Eindhoven (NL)

(72) Inventors: Toon Hendrik Evers, Eindhoven (NL); Maatje Koets, Wageningen (NL)

(73) Assignee: Koninklijke Philips N.V., Eindhoven (NL)

( * ) Notice: Subject to any disclaimer, the term of this patent is extended or adjusted under 35 U.S.C. 154(b) by 813 days.

(21) Appl. No.: 14/358,550

(22) PCT Filed: Nov. 13, 2012

(86) PCT No.: PCT/IB2012/056378
§ 371 (c)(1),
(2) Date: May 15, 2014

(87) PCT Pub. No.: WO2013/072842
PCT Pub. Date: May 23, 2013

(65) Prior Publication Data
US 2015/0177239 A1  Jun. 25, 2015

Related U.S. Application Data

(60) Provisional application No. 61/560,441, filed on Nov. 16, 2011.

(30) Foreign Application Priority Data

Nov. 16, 2011 (EP) ..................................... 11191454

(51) Int. Cl.
*G01N 33/543* (2006.01)
*G01N 21/00* (2006.01)
(Continued)

(52) U.S. Cl.
CPC ....... *G01N 33/54393* (2013.01); *G01N 21/00* (2013.01); *G01N 33/54326* (2013.01);
(Continued)

(58) Field of Classification Search
CPC ....... G01N 33/54333; G01N 33/54353; G01N 33/54393; G01N 33/74; G01N 33/54326;
(Continued)

(56) References Cited

U.S. PATENT DOCUMENTS 5,849,878 A * 12/1998 Cantor ............... C07K 16/2809
530/387.3
9,612,236 B2 * 4/2017 Sabatte .............. G01N 33/5306
(Continued)

FOREIGN PATENT DOCUMENTS

EP  1441217 A2  7/2004
WO  2008072156 A2  6/2008
(Continued)

OTHER PUBLICATIONS

Anthony S. Ham, "Action at a Distance: Lengthening Adhesion Bonds with Poly(ethylene glycol) Spacers Enhances Mechanically Stressed Affinity for Improved Vascular Targeting of Micoparticles", Langmuir 2009, 25 (17) pp. 10038-10044. American Chemical Society, Published on Web Jul. 2009, DOI: 10.1021/la900966h.
(Continued)

*Primary Examiner* — Gailene Gabel

(57) ABSTRACT

A device detects a target molecule in a sample in a sample container to measure the target molecule. A first particle is functionalized with a first binding molecule capable of specifically binding to said target molecule. A surface structure includes a second binding molecule. The surface structure covers a flat sensor or is present on a second particle. The first particle is capable of binding the second binding molecule of the surface structure directly or indirectly. The
(Continued)

first and/or second binding molecule is indirectly attached to the particle surface of the first and/or second particle and/or the flat sensor surface via a long and rigid linker molecule. A length and a consistency of the linker molecule is selected such as to result in an average extension length of the linker of more than 60 nm. A number of particle clusters or of bound particles is directly or inversely related to an amount of the target molecules present in the sample.

19 Claims, 8 Drawing Sheets

(51) Int. Cl.
  *G01N 33/68* (2006.01)
  *G01N 33/553* (2006.01)
  *G01N 33/74* (2006.01)

(52) U.S. Cl.
  CPC . *G01N 33/54353* (2013.01); *G01N 33/54366* (2013.01); *G01N 33/553* (2013.01); *G01N 33/6887* (2013.01); *G01N 33/74* (2013.01); *G01N 2333/58* (2013.01)

(58) Field of Classification Search
  CPC .......... G01N 33/54366; G01N 33/553; G01N 33/6887; G01N 21/00; G01N 21/552; G01N 2333/58
  See application file for complete search history.

(56) References Cited

U.S. PATENT DOCUMENTS

| | | | |
|---|---|---|---|
| 2002/0172963 A1* | 11/2002 | Kelley | B01J 23/75 506/39 |
| 2004/0033624 A1 | 2/2004 | Zweig | |
| 2004/0038316 A1* | 2/2004 | Kaiser | C07H 21/00 435/7.2 |
| 2004/0110220 A1 | 6/2004 | Mirkin et al. | |
| 2004/0241748 A1* | 12/2004 | Ault-Riche | G01N 33/54353 435/7.1 |
| 2005/0048599 A1 | 3/2005 | Goldberg et al. | |
| 2006/0046255 A1 | 3/2006 | Buchardt et al. | |
| 2006/0057578 A1* | 3/2006 | Willner | C12Q 1/6804 435/6.11 |
| 2008/0299565 A1* | 12/2008 | Schneider | C12Q 1/6818 435/6.14 |
| 2009/0148863 A1 | 6/2009 | Xu et al. | |
| 2009/0258355 A1* | 10/2009 | Maye | B82Y 5/00 435/6.12 |
| 2010/0008618 A1 | 1/2010 | Swanson | |
| 2011/0275061 A1* | 11/2011 | Weidemaier | G01N 21/658 435/6.1 |
| 2012/0025005 A1 | 2/2012 | Smith | |
| 2012/0202194 A1 | 8/2012 | Evers | |
| 2013/0095495 A1* | 4/2013 | Sabatte | G01N 33/54306 435/6.12 |
| 2013/0216506 A1* | 8/2013 | Discher | C12M 47/04 424/93.7 |
| 2014/0127722 A1* | 5/2014 | Ranzoni | G01N 33/54326 435/7.92 |

FOREIGN PATENT DOCUMENTS

| | | |
|---|---|---|
| WO | 2008083323 A1 | 7/2008 |
| WO | 2009005552 A2 | 1/2009 |
| WO | 2010073182 A1 | 7/2010 |
| WO | 2011036597 A1 | 3/2011 |

OTHER PUBLICATIONS

Peter E. Nielsen et al, "An Introduction to Peptide Nucleic Acid", Current Issues Molec. Biol. (1999) 1 (2): pp. 89-104.

Buddy D. Ratner et al, "Biomaterials Science: A Multidisciplinary Endeavor", Biomaterials Science, 2nd Ed; Elsevier: London, 2004, pp. 1-20.

Veronique Jarrige et al, "A fast intraoperative PTH point-of-care assay on the Philips handheld magnotech system", Langenbeck's Archives of Surgery, Springer, Berlin, De., vol. 398, No. 3, Dec. 21, 2010, pp. 337-343.

Andrea Ranzoni et al, "Frequency-Selective Rotation of Two-Particle Nanoactuators for Rapid and Sensitive Detection of Biomolecules", NANO Letters 2011, 11, ACS Publications pp. 2017-2022.

D.M. Bruls et al, "Rapid integrated biosensor for multiplexed immunoassays based on actuated magnetic nanoparticles", Lab on Chip, Royal Society of Chemistry, vol. 9, No. 24, Oct. 15, 2009, pp. 3504-3509.

Jeroen Nieuwenhuis, "Magnotech: Reliable and Fast Magnetic Point-of-Care Biosensor Technology", 41st Annual Oak Ridge Conference—2009, Apr. 16, 2009, pp. 1-10. XP002610327.

Ross Stewart, "The Proton: Applications to Organic Chemistry", Academic Press, 1985. pp. 72-74.

\* cited by examiner

LONG RIGID SPACERS TO ENHANCE BINDING KINETICS IN IMMUNOASSAYS

CROSS-REFERENCE TO PRIOR APPLICATIONS

This application is the U.S. National Phase application under 35 U.S.C. § 371 of International Application No. PCT/IB2012/056378, filed on Nov. 13, 2012, which claims the benefit of U.S. Provisional Patent Application No. 61/560,441, filed Nov. 16, 2011 and European Patent Application No. 11191454.5, filed on Nov. 16, 2011. These applications are hereby incorporated by reference herein.

FIELD OF THE INVENTION

The present invention relates to a device for detecting a target molecule within a sample comprising a sample container for the measurement of the target molecule within a sample, a first particle, wherein said first particle is functionalized with a first binding molecule capable of specifically binding to said target molecule, and a surface structure comprising a second binding molecule, wherein said surface structure covers a flat sensor or is present on a second particle, wherein said first particle is capable of binding said second binding molecule of the surface structure directly or indirectly; wherein said first and/or second binding molecule is indirectly attached to the particle surface of said first and/or second particle and/or the flat sensor surface via a long and rigid linker molecule; wherein the length and the consistency of said linker molecule is selected such as to result in an average extension length of said linker of more than 60 nm; and wherein the number of particle clusters or of bound particles is directly or inversely related to the amount of target molecules present in the sample. In a further aspect the present invention relates to a method of detecting the presence or amount of a target molecule within a sample. The present invention also describes the use of a particle according to the invention for detecting a target molecule within a sample.

BACKGROUND OF THE INVENTION

The demand for pervasive and effective healthcare moves the world of in vitro diagnostics towards integrated random-access and point-of care solutions. The achievement of such solutions is demanding: the tests needs to be rapid, sensitive, quantitative and accurate. Moreover the platform on which the test is performed need to be easy to use and compact.

Affinity assays make use of biological molecules to capture specific target molecules from a sample and allow a determination of their concentration. Typically, affinity capture is achieved by dispersing nano- or microparticles coated with capture molecules into sample fluid (Luchini et al., 2008, Nano Lett., 8(1), 350-361). Typical affinity-based assays are therefore used in a huge number of applications such as diagnostic assays, detection of biomolecules in research such as proteins, peptides and nucleic acids thereby making use of affinity molecules such as, e.g. antibodies, which are typically characterized by a high binding affinity towards a specific biomolecule. In principle, the functionalized magnetic particles are attracted to a sensor surface, where the particles can indirectly, i.e. by virtue of a captured analyte or directly bind to capture probes such as antibodies printed on the surface. The number of bound particles is directly or inversely related to the amount of target molecules present I the sample. Typically, in such biosensor applications, the particles can be detected using any technique sensitive to particle close at the surface, often such techniques are based on optical detection such as the detection of scattered light or frustrated total internal reflection (FTIR) as described for instance in Bruls et al., Lab Chip, 2009, 9. 2504-3510.

WO 2008/0833 A1 discloses methods, reagents and apparatuses for the detection of agents. Assay formats for the detection of one or more agents of interest in a sample based on conventional direct and indirect sandwich assays are described.

US 2004/110220 A1 discloses methods and devices for detecting nucleic acids. In particular, the detection system is mainly based on nanoparticles having oligonucleotides attached thereto (nanoparticle-oligonucleotide conjugates). The oligonucleotides described therein have a portion that is complementary to a portion of the sequence of the nucleic acid (recognition portion) to allow hybridization to a target nucleic acid.

WO 2009/005552 A2 describes methods and compositions for multivalent binding and quantitative capture of components in a sample. In particular, modification of conventional sandwich assay formats so as to result in polyvalent "avidity" binders to increase the apparent Kd are described. This is achieved by affixing more than one antibody or antigen to a "scaffold" which may be backbone polymer such as a single or double stranded nucleic acid such as PNA, DNA, RNA, etc.

US 2009/148863 discloses detection platforms based on functionalized nanoparticles. In particular, the nanoparticles comprise a first monolayer components which is adapted to bind to a biological moiety, which in turn can be adapted to bind to an analyte. The nanoparticle surface can further comprise a second monolayer component, which contributes to the exposure of the first monolayer component on the surface. The nanoparticles are bound via a first and second monolayer to a capture molecule, e.g. an antibody, which allow single molecule detection in real time.

EP 1441217A2 describes a optical waveguide binding assay based on the detection of scattering of light directed into TIR elements or waveguide devices through immobilization of specific binding members (SBM) by various means.

US 2005/0048599 discloses the detection of microorganisms on a fixed substrate. Binding is based on the provision of a sandwich configuration and occurs via a tag binding component that binds the tag to the target through a means that is specific to a target (e.g. antibodies or aptamers). An indicator component is detectable by a detector.

An important drawback of the affinity-assays of the prior art, however, is the fact that the binding of the functionalized particles having bound a target molecule to the surface is still very slow, rate-limiting and inefficient. One reason for this slow reaction inter alia lies in the difficulty of binding a relatively large (e.g. ~500 nm) particle to a surface via a small (e.g. ~10 nm) target molecule. The disproportion is sketched in FIG. 3 illustrating the relative sizes of target and particle. As a consequence, there exist not many orientations of the particle-target complex which result in a efficient binding. Although the particle can rotate when being in contact with the surface, the binding probability is nevertheless rather small.

There is thus a strong need to design novel particle-target structures, which are capable of efficiently binding to a surface such as a flat sensor surface or a particle surface.

OBJECTS AND SUMMARY OF THE INVENTION

The present invention addresses these needs and provides means for enhancing the binding efficiency of particles to surfaces. The above objective is in particular accomplished by a device for detecting a target molecule within a sample comprising a sample container for the measurement of the target molecule within a sample, a first particle, wherein said first particle is functionalized with a first binding molecule capable of specifically binding to said target molecule, and a surface structure comprising a second binding molecule, wherein said surface structure covers a flat sensor or is present on a second particle, wherein said first particle is capable of binding said second binding molecule of the surface structure directly or indirectly; wherein said first and/or second binding molecule is indirectly attached to the particle surface of said first and/or second particle and/or the flat sensor surface via a long and rigid linker molecule; wherein the length and the consistency of said linker molecule is selected such as to result in an average extension length of said linker of more than 60 nm; and wherein the number of particle clusters or of bound particles is directly or inversely related to the amount of target molecules present in the sample.

The invention describes how the binding probability of a large particle to a surface can be significantly increased by attaching the target to the particle linker molecules having a certain length. Surprisingly, it could be observed that the provision of a long and rigid linker or spacer molecule overcomes the binding difficulties of the particles as used in the prior art and thus enables a more effective binding.

FIG. 4 illustrates the principle underlying the present invention. The number of possible orientations in which a particle can bind to the surface strongly increases if the attachment point is positioned further away from particle. The use of a long spacer molecule does however not necessarily solve the problem. FIG. 5 illustrate that even if a very long linker is used, e.g. a PEG-molecule, the flexibility of the molecule would rather lead to a fold up resulting in a globular structure and thus a minor extension of the capture molecule from the particle surface.

Without wishing to be bound to a theory, one explanation for the observed increased binding efficiency is that the use of a long and rigid linker molecules for positioning a binding molecule away from the particle surface significantly enhances the kinetics of binding a particle to the surface. The inventors of the present application have recognized that the resulting end-to-end-distance is a function of the average extension length, contour length and rigidity of a molecule and could demonstrate that these characteristics significantly contribute to the observed enhance binding kinetics.

In an experiment using 500 nm streptavidin coated nanoparticles and rigid dsDNA molecules as linker molecules of varying length, it could, in particular, be shown that the number of bound particles increases with dsDNA-linker length (see FIG. 6). In particular, the inventors could demonstrate that the length of the linker molecules on the particles essentially contributes to the number of bound particles at a sensor surface. These findings and other finding which will be described in detail herein have lead to the development of an improved linker design. Hence, the linker architecture as described herein is responsible for the enhanced binding kinetics thus improving the speed, efficacy and accuracy of nanoparticle based affinity assays In a preferred embodiment of the present invention the first and/or second particle is a magnetic particle.

In a further preferred embodiment, the diameter of said first and/or second particle is at least about 100 nm. In further preferred embodiments, the average extension length of a linker as mentioned above is at least 10% of the diameter of a particle having a diameter of at least about 100 nm In yet another preferred embodiment, said rigid linker molecule has an average extension length of at least 20% of the contour length of said linker molecule.

In another preferred embodiment of the present invention, the first binding molecule is an antibody or a fragment thereof, an aptamer, a ligand, or a complementary nucleic acid.

In a specific embodiment of the present invention the rigidity and length of said linker molecule is determined via the root mean square end-to end distance of the linker $\sqrt{<R^2>}$, where $<R^2>$ can be described according to the formula $$<R^2>=2Pl[1-(P/l)(1-e^{-l/P})],$$

wherein P is the persistence length of the polymer and l is the contour length of the linker.

In a preferred embodiment of the present invention, the linker molecule is or comprises a nucleic acid molecule or a non-biological polymer. In a particularly preferred embodiment the linker molecule may be selected from the group consisting of a double-stranded nucleic molecule such as dsDNA, a PNA molecule, a PNA-DNA duplex, and an RNA-DNA duplex.

In yet another particularly preferred embodiment the double-stranded nucleic acid molecule is a dsDNA, a PNA-DNA duplex, or an RNA-DNA duplex.

In the most preferred embodiment of the present invention the linker molecule is a dsDNA.

In another preferred embodiment of the present invention the first particle additionally comprises a repulsive surface structure which is directly attached to the surface of said particle, wherein said repulsive surface structure covers the surface of the particle so as to result in a specific net charge and/or a steric repulsion of the particle, and wherein said repulsive surface structure conveys a pushing effect on said particles towards said sensor surface.

In yet another preferred embodiment of the present invention the linker molecule is longer than said repulsive surface structure.

In a further preferred embodiment of the present invention said repulsive surface structure is a charged structure.

In a particularly preferred embodiment the charged structure is or comprises a molecule selected from the group consisting of a nucleic acid such as a double stranded nucleic acid, e.g. dsDNA, a PNA, a PNA-DNA duplex, an RNA-DNA, a hydrogel, and a polymer.

In a further particularly preferred embodiment of the present invention, said repulsive surface structure is a steric coating.

In another preferred embodiment of the present invention the linker molecule and/or said repulsive surface structure is not cleavable by DNase and/or a restriction enzyme capable of cutting a double stranded nucleic acid molecule.

In another preferred embodiment of the present invention, the linker molecule further comprises at least one short flexible spacer.

In yet another preferred embodiment the short flexible spacer comprises a single stranded nucleic acid.

The present invention in a further aspect relates to a method of detecting the presence or amount of a target molecule within a sample comprising the steps of (a) contacting the sample and a first binding molecule attached to a first particle in a device according to the present invention; and
   (b) contacting the sample with
      i) a second binding molecule capable of attaching to a flat surface or to a second particle, wherein the first binding molecule and/or the second binding molecule are capable of specifically binding to said target molecule, or
      ii) a target analog molecule attached to the flat surface or to the second particle; wherein the target molecule is capable of interfering with the binding of the first binding molecule to the target analog molecule; and
   (c) detecting the number of first particles bound to the flat surface or to the second particle by virtue of the binding of the first binding molecule to the second binding molecule,
wherein the number of particle clusters or of bound particles is directly or inversely related to the amount of target molecules present in the sample.

In a further preferred embodiment of the present invention, a magnetic force is applied to bring the particles into close proximity with said solid support or to each other so as to facilitate clustering of the particles.

In a further preferred embodiment of the present invention, the attachment of said second binding molecule to the flat surface or the second particle occurs prior or after the binding of the second binding molecule to the target molecule.

In another preferred embodiment of the present invention, the detection of bound particles occurs via frustrated total internal reflection (FTIR) or via measurement of scattered light from said bound particles near the surface or via the optical detection of cluster formation.

In a further aspect, the present invention describes the use of a particle as defined herein for detecting a target molecule within a sample.

In a particularly preferred embodiment of the present invention, the target molecule as mentioned in the context of the device, method or use as described herein above is cardiac troponin I (cTnI), NT-proBNP or parathyroid hormone.

DETAILED DESCRIPTION OF THE EMBODIMENTS

Figure 1:
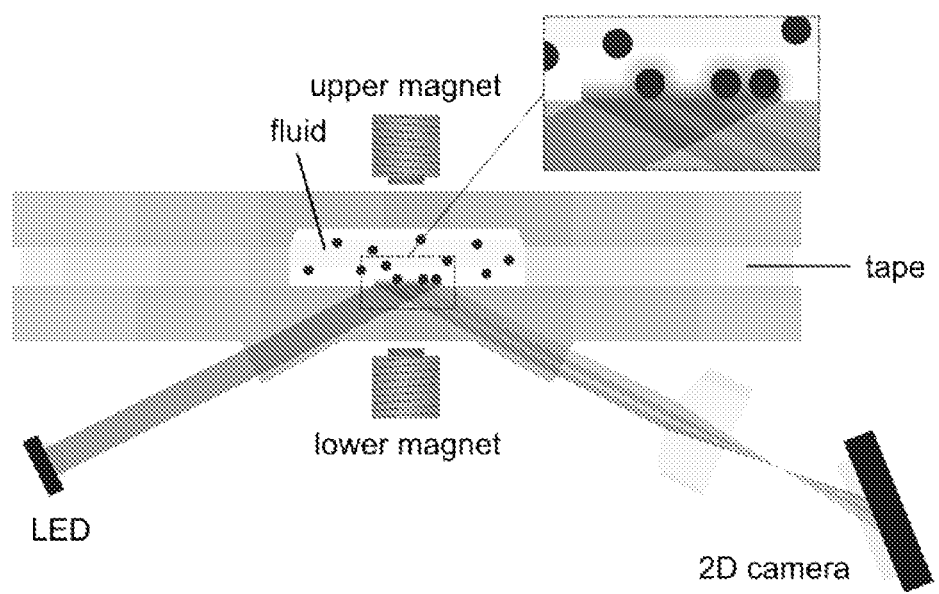
FIG. 1 shows the principle of FTIR detection. Light from a light source enters a cartridge, is reflected from the cartridge/fluid interface and imaged on a detector. If particles are present in the evanescent field, created on this interface, the reflected light intensity decreases.

The present invention relates to a means and methods for detecting a target molecule within a sample. Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a device for detecting a target molecule within a sample comprising a sample container for the measurement of the target molecule within a sample, a first particle, wherein said first particle is functionalized with a first binding molecule capable of specifically binding to said target molecule, and a surface structure comprising a second binding molecule, wherein said surface structure covers a flat sensor or is present on a second particle, wherein said first particle is capable of binding said second binding molecule of the surface structure directly or indirectly; wherein said first and/or second binding molecule is indirectly attached to the particle surface of said first and/or second particle and/or the flat sensor surface via a long and rigid linker molecule; wherein the length and the consistency of said linker molecule is selected such as to result in an average extension length of said linker of more than 60 nm; and wherein the number of particle clusters or of bound particles is directly or inversely related to the amount of target molecules present in the sample.

Envisaged by the present invention is a suitable device, preferably for detection of a target molecule using a bio sensor system. Various analytical procedures to detect the presence and/or quantity of an analyte in a test sample or sample volume are known in the art. Typically, such a detection system may optically detect particles, which are functionalized with a suitable binding molecule in order to bind the analyte of interest. The presence or quantity of the analyte may be concluded from the number of analyte bound to the particles. The presence or quantity of the analyte may be also concluded from the number of particle clusters. In specific embodiments of the present invention, the biosensor system comprising the device as described herein may be capable of detecting single particles bound to a flat sensor as described herein or the presence of particle cluster, and actuating the particles by a magnetic field generated by a magnetic field generator.

A "magnetic field generator" as used herein typically comprises one or more magnets within the optomagnetic device as described herein for generating a magnetic field with the sample chamber, wherein said magnetic field shall guide magnetic particles towards the contact surface. The magnetic field will typically have a nonzero gradient that allows to exert magnetic forces on magnetic (dipole) particles. Suitable examples of such magnetic field generators, or suitable systems comprising such magnetic field generators would be known to the person skilled in the art. In specific embodiments of the present invention the magnetic field generator may be a magnetic field generator as described in Bruls et al., Lab Chip, 2009, 9. 2504-3510, or be comprised in or be part of a system as described in Ranzoni et al., 2011, Nano Lett., 11, 2017-2022.

Figure 2:
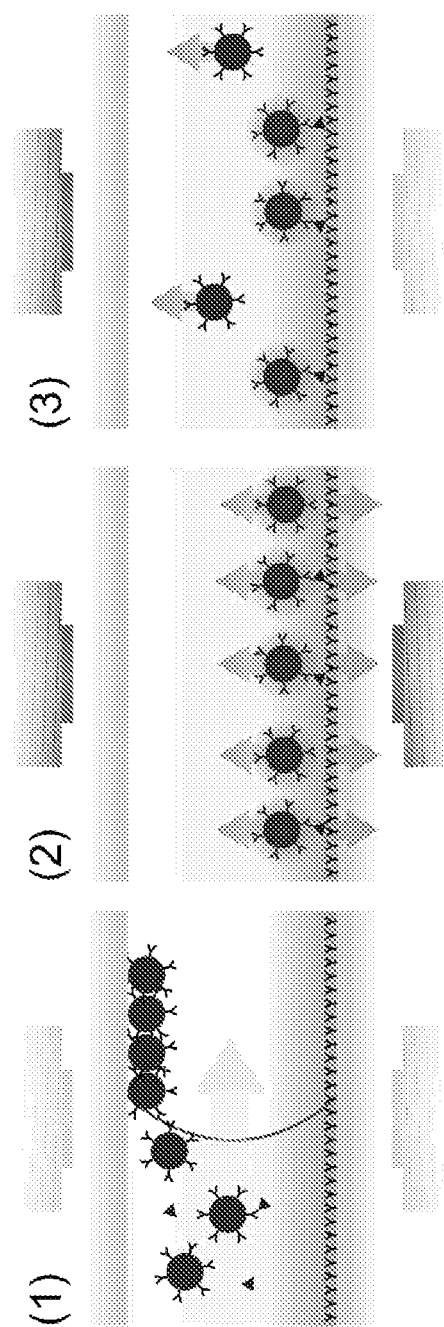
FIG. 2 shows a sandwich immunoassay using Magnotech technology. In panel (1) magnetic particles coated with a primary antibody directed against the target disperse in the sample liquid and bind the target. In panel (2) top and bottom coils actuate the magnetic particles in a pulsed manner, resulting in binding to the sensor surface where a secondary antibody can bind to the bound target molecule. In panel (3) non-bound particles are removed from the sensor surface and bound particles are detected using an evanescent field.
Figure 3:
FIG. 3 illustrates the relative sizes of a 10 nm target molecule (black), sandwiched between the sensor surface and a 500 nm particle (not fully displayed). Left: particle properly oriented to form a bond; right: particle not properly oriented to form a bond.

Typically, the magnetic particles can be actuated by applying a magnetic field such that the analytical procedure can be accelerated. In specific embodiments of the present invention, it is also envisaged that the use of a magnetic field may reduce the background signal due to removal of unspecifically bound particles. FIG. 2 shows one example of how particles may be actuated to effectively remove unspecifically or non-bound particles from the flat sensor as described herein. A top and bottom magnet which may be actuated in a pulsed manner efficiently remove non-bound particles so that the bound particles are detected at the sensor surface.

A magnetic actuation as used in the context of the present invention may be used differently, namely to arrange magnetic particles in a sample into chains in order to accelerate clustering of particles. It is also envisaged by the present invention to use magnetic actuation to vibrate and rotate particle clusters for the determination of the presence and amount of formed clusters. In specific embodiments the magnetic actuation of the particles may occur as pulsed, i.e. the actuation field is at least once interrupted by a pause. The dynamic actuation in terms of repeated pulses has been found to reduce non-specific interactions and enhance the number of binding events. Further details and parameters regarding the detection of a target molecule using based on the detection of particle clusters would be known to the person skilled in the art or can be derived from Ranzoni et al., 2011, Nano Lett., 11, 2017-2022.

Biosensor systems suitable for use in the present invention may comprise, for example, a biosensor cartridge comprising a sample container, a sensor device for sensing the particles, detection system, and optionally a magnetic field generator. The systems may, in further embodiments, comprise one or more additional functional units such as a readout system, e.g. a screen or printer, an interface for database or computer systems, a calibration unit, a direct or indirect connectivity with high-throughput devices etc. Particularly envisaged by the present invention are handheld devices for quick and instant analysis where a cartridge including the assay format may be inserted. Typically, such a device comprises a power supply, preferably in form of rechargeable batteries, a display, wireless connectivity such as WLAN for quick database access, or access to a laboratory information system. An exemplary bio sensor system, which may be used in the context of the present invention, is described in Bruls et al., Lab Chip, 2009, 9. 2504-3510.

Particularly preferred are sensing devices based on an optical detection of particles near or at a surface. Without being limited thereto, an exemplary device is illustrated in FIG. 1 comprising a light source and a light detection system.

A "sample" as used herein refers to any sample, which includes a target molecule as defined herein. Such samples may, for example, include samples derived from or comprising stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, e.g. from all suitable organs, e.g. the lung, the muscle, brain, liver, skin, pancreas, stomach, etc., a nucleated cell sample, a fluid associated with a mucosal surface, hair, or skin. In addition, samples from environmental sources, e.g. water samples, meat or poultry samples, samples from sources of potential contamination etc. may be used.

The term "target molecule" as used herein refers to any molecule bound by a binding molecule and may for example be a biological substance such as a biomolecule, preferably a biomarker, complexes, cell fractions or cells. Preferably, a target molecule within the context of the present invention is a nucleic acid, e.g. DNA, or RNA molecule or an oligonucleotide such as a DNA or RNA oligonucleotide. Even more preferred are target molecules such as a peptide, a polypeptide or protein, a protein or polypeptide fragment, or functional protein or polypeptide domain, a drug molecule, a small molecule, or a vitamin.

A target molecule may be directly obtained from the samples as described herein above. In other situations samples may be subjected to sample preparation techniques, e.g. based on standard protocols, including, for example, partial purification, which renders the target molecules more accessible to binding partners, i.e. an affinity molecule as defined herein. For example, blood samples may be centrifuged to separate fractions including whole cells or membranes from serum, feces samples may be sectioned and homogenized with physiologically acceptable buffer and detergent, sputum samples may be liquefied and fractionated. Furthermore, antibiotics or bactericides may be added to samples to prevent further growth of any organisms present. Whole cells may also be removed or may be lysed to release their contents.

A "sample container" as used herein refers to a container made from any suitable material like glass, any transparent plastic, or a semiconductor in which the sample is measured. The magnetic particles as described herein may be already present in the sample container when the sample is introduced, be introduced together with the sample, or be introduced after the sample has been injected into the sample container. The sample container may further comprise a sensor surface comprising a second binding molecule. Preferably, the sensor surface is located at the bottom of the sample container. The sample container may, in specific embodiments, be located within an exchangeable cartridge, e.g. in a standalone component separate from the sensor device. Due to possible contamination with a sample, such a cartridge may preferably be a disposable item, made for instance from plastics by injection molding. Also envisaged are recyclable cartridges or recyclable cartridge parts, e.g. cartridges or cartridge parts, which can be cleansed or sterilized.

A "flat sensor" as used herein, defines an area at which an actual sensor event occurs or is detected. Typically, the flat sensor is located at the bottom of the sample container. The flat sensor may serve for the detection of the number of bound particles, which is directly or inversely related to the amount of target molecules present in the samples. Examples of such flat sensors and corresponding sensors, which may be used in the context of the present invention are provided in Bruls et al., 2009, Lab Chip, 9, 3504-3510.

The term "particle" as used herein means a small, localized object to which can be ascribed a physical property such as volume or mass. In the context of the present invention a particle comprises or consists of any suitable material known to the person skilled in the art, e.g. the particle may comprise, or consist of, or essentially consist of inorganic or organic material. Typically, a particle may comprise, or consist of, or essentially consist of metal or an alloy of metals, or an organic material, or comprise, or consist of, or essentially consist of carbohydrate elements. Examples of envisaged material include agarose, polystyrene, latex, polyvinyl alcohol, silica and ferromagnetic metals, alloys or composition materials. Particularly preferred are magnetic or ferromagnetic metals, alloys or compositions. Particularly preferred particles useful in the present invention are superparamagnetic particles. The term "superparamagnetic" as used herein describes a form of magnetism, which appears in small ferromagnetic or ferromagnetic nanoparticles. It is known in the art that in sufficiently small nanoparticles, magnetization can randomly flip direction under the influence of temperature. The time between two flips is referred to as the Néel relaxation time. In the absence of an external magnetic field, when the time used to measure the magnetization of the nanoparticles is much longer than the Néel relaxation time, the magnetization appears to be in average zero, i.e. in the paramagnetic state. In such a state an external magnetic field is able to magnetize the nanoparticles similarly to a paramagnet. However, the magnetic susceptibility is much larger than those of paramagnets. In further preferred embodiments, the material may have specific properties. The material may, for example, be magnetic or be non-magnetic. The material may, in other embodiments, be hydrophobic, or hydrophilic. In further specific embodiments the particle is a plastic particle. Examples of plastic particles include latex or polystyrene beads, e.g. those commonly used for purification. In yet another embodiment, the particle may be a cell like particle. The term "cell like particle" as used herein refers to a biological or semi-biological structure, which is present in biological systems or has the form and/or function of biological systems or parts of biological systems. A preferred example or a cell like particle is a liposome.

The term "liposome" as used herein means a vesicle, e.g. comprising a lipid or phospholipid membrane or layer, e.g. bilayer. Typically, liposomes are hollow structures, which can be filled with molecules, e.g. drug molecules or pharmaceutical compositions, and be used to deliver such molecules to target sites, e.g. cancer cells or infected areas etc. Liposomes may preferably be composite structures made of phospholipids and may contain small amounts of other molecules, e.g. be composed of naturally derived phospholipids with mixed lipid chains (like egg phosphatidyl ethanolamine) or other surfactants. A liposome may vary in size from a nanometer range to tens of micrometers. In further specific embodiments, a particle may comprise, essentially consist of or consist of sepharose or agarose.

Furthermore, a particle essentially behaves as a whole unit in terms of its transport and properties. Particles may accordingly be of a symmetrical, globular, essentially globular or spherical shape, or be of an irregular, asymmetric shape or form.

The size of a particle envisaged by the present invention typically ranges between 50 nm and 50 µm. Preferred are particles in the nanometer and micrometer range up to several micrometers. In further preferred embodiments the particle diameter is larger than 100 nm. The term "diameter" as used herein refers to any straight line segment that passes through the center of the particle and whose endpoints are on the particle surface. In case of non-spherical or semi spherical particles, the diameter is understood as the average diameter of the largest and shortest straight line segments that pass thought the center of the particle and whose endpoints are on the particle surface. It is further understood that a radius of a particle as defined herein is half of its diameter as defined herein above. Particularly preferred are nanoparticles, e.g. particles of a diameter of about 100 nm to 10 micrometer, more preferably 100 nm to 3 µm, even more preferably 300 nm to 1000 nm, e.g. 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 620 nm, 650 nm, 670 nm, 700 nm, 720 nm, 750 nm, 770 nm, 800 nm, 820 nm, 850 nm, 870 nm, 900 nm, 920 nm, 950 nm, 970 nm, 1000 nm, or any value in between. Even more preferred are nanoparticles having a diameter of about 500 nm.

Preferably, the particles according to the present invention are functionalized with a first binding molecule or a second binding molecule. Envisaged by specific embodiments of the present invention are also particles further comprising a charged structure as described herein.

In a particularly preferred embodiment, the material is a magnetic material. In further particularly preferred embodiments, the entity on which a surface structure as defined herein above is present, or on which a first or second binding molecule according to the present invention is attached to is a magnetic nanoparticle.

In particularly preferred embodiments of the present invention, the material, or particle, e.g. nanoparticle may be superparamagnetic particles, which are typically dispersed in aqueous solutions and retain a small charge, e.g. a negative or positive charge, or possess a certain zeta potential to ensure colloidal stability, keeping the particles separated and avoiding non-specific clustering.

Envisaged by the present invention are at least two types of particles, namely a first and second particle.

The term "first particle" as used herein refers to a particle as described herein which is functionalized with a first binding molecule. The first binding molecule can be any molecule capable of specifically binding to a target molecule of interest. The first particle thus functions as a capture particle. The first binding molecule may be attached to the surface indirectly via a long and rigid linker molecule as defined herein. The surface of the first particle can be further modified by additional structures such as a charged structure as described herein.

The term "second particle" as used herein refers to a particle as described herein which are, which is functionalized with a second binding molecule. Envisaged by the present invention is that the second particle comprises a surface structure as described herein comprising a second binding molecule. Also envisaged by the present invention is that the second particle may bind to the first particle by virtue of the binding of the target molecule. The second particle is thus capable of binding the target molecule via binding of the second the second binding molecule. The envisaged binding of the first particle having captured the target molecule to the second particle leads to formation of particle cluster, which can be detected as described herein. The number of particle clusters is then directly or inversely related to the amount of target molecules present in the sample.

The term "binding molecule" as used herein refers to any molecule having a high binding affinity for a second molecule, i.e. an interaction partner. A binding molecule in the sense of the present invention typically comprises binding or capture moieties capable of binding a specific target molecule as defined herein such as a biomolecule or a biomarker, or capable of binding a molecule-containing target entity, such as for example a virus, or a cell or a cell fragment, or material derived from tissue.

In a particularly preferred embodiment, the binding molecule is selected from the group consisting of aptamers, peptides, proteins, oligonucleotides, in particular complementary nucleic acids, and molecular imprinted polymers, ligands or receptors, and lectins, wherein the binding molecule preferably is an antibody or a fragment thereof or a complementary nucleic acid.

An "aptamer" as used within the context of a binding molecule may be a short nucleic acid molecule, e.g. an RNA, DNA, or PNA molecule or any other suitable nucleic acid format known to the person skilled in the art, being capable of binding to a target molecule as defined herein, preferably to a nucleic acid target molecule as defined herein. Furthermore, the present invention envisages peptide aptamers, i.e. aptamers, which are able to specifically bind to (a) protein (s), polypeptide(s) or peptide(s) comprising a specific amino acid sequence(s). Typically, (a) peptide aptamer(s) is/are a variable peptide loop(s), comprising for example 10 to 20 amino acids. In the context of the present invention the peptide aptamer(s) may in specific embodiments be attached at one or both ends to a scaffold structure. The scaffold structure may be any molecule, preferably a protein, e.g. a protein, which has good solubility properties. Suitable scaffold molecules would be known to the person skilled in the art. An example of a suitable scaffold molecule to be used in the context of the present invention is the bacterial protein thioredoxin-A. The aptamer peptide loop may preferably be inserted within a reducing active site of the scaffold molecule. Alternatively, staphylococcal protein A and domains thereof and derivatives of these domains, such as protein Z or lipocalins may be used as scaffold structures in the context of the present invention. Nucleic acid or peptide aptamers may be generated according to any suitable method known to the person skilled in the art, e.g. via PCR or molecular synthesis approaches or yeast two-hybrid approaches.

A "peptide" consists of amino acids chains. A peptide as used within the context of a binding molecule may comprise or alternatively consist of a stretch of 2 to 35 amino acids, amino acid derivatives or a mixture thereof. The peptide may be linear, branched, circular or mixture thereof. A peptide affinity molecule may also be attached to a scaffold structure as defined herein above.

A "protein" is a polymer of amino acids linked by peptide bonds, which may comprise one polypeptides chain or more than one polypeptide chain put together typically in a biologically functional way. A protein as used within the context of binding molecule may comprise or alternatively consist of a stretch more than about 35 amino acids, amino acid derivatives or a mixture thereof. The protein may have a linear, branched, circular form or be comprised of a mixture of these forms. A protein binding molecule may also be attached to a scaffold structure as defined herein above.

An "oligonucleotide" as used within the context of a binding molecule may comprise or alternatively consist of a stretch of about 5 to 120 nucleotides, e.g. a stretch of 10, 20, 30, 40, 50, 60, 70, 80, 90 or 100 nucleotides, preferably of about 15 to 60 nucleotides.

An oligonucleotide binding molecule may preferably be an RNA, DNA or PNA molecule, or a mixture thereof. Envisaged are binding molecules, which are complementary nucleic acid molecules. The term "complementary nucleic acid molecule" refers to a molecule of a defined sequence, where the single strands are complementary to each other. It is known in the art that complementary strands of a double stranded nucleic acid molecule have a strong affinity to each other due to the formation of base pairing. Also envisaged are single stranded oligonucleotide sequences, which are attached to or integrated into the linker molecule structure as defined herein. In particularly preferred embodiments such suitable linker also comprise of consist a nucleic acid molecule. The single stranded stretch is capable of recognizing and hybridizing to the complementary nucleotide sequence of interest with high affinity. In such an analysis the target molecule comprises an oligonucleotide that is complementary or almost complementary to the binding molecule.

The term "molecular imprinted polymer" as used herein refers to a polymer, which was formed in the presence of a molecule that is extracted afterwards, leaving complementary cavities behind. Typically, a molecular imprinted polymer shows a certain chemical affinity for the original molecule. A molecular imprinted polymer may be composed of any suitable polymeric unit known to the person skilled in the art. Techniques for their production include polymerization techniques such as bulk, precipitation, emulsion, suspension, dispersion, gelation, and multi-step swelling polymerization. Particularly preferred are hierarchical imprinting methods.

An "antibody" as used within the context of a binding molecule refers to an immunoglobulin molecules and immunologically active portions of immunoglobulin molecules, i.e. molecules that contain an antigen binding site that immunospecifically binds an antigen. The immunoglobulin molecules of the invention can be of any type (e.g., IgG, IgE, IgM, IgD, IgA and IgY), class (e. g., IgG1, IgG2, IgG3, lgG4, lgA1 and IgA2) or subclass of immunoglobulin molecules. Antibodies of the present invention may be described or specified in terms of the epitope(s) or portion(s) of a target molecule, e.g. polypeptide of the present invention, which they recognize or specifically bind. Specific epitopes and their interaction with antibodies would be known to the person skilled in the art. The term "specifically binding" as used herein refers to the immunospecific detection and binding of an antibody to an antigenic epitope. The term "specifically binding" excludes non-specific binding but does not necessarily exclude cross-reactivity with other antigens, in particular with antigens comprising the same antigenic epitope detected by the present antibody.

The antibody may be a polyclonal, monoclonal, multi-specific, human, humanized or chimeric antibody, single chain antibody, or constitute a Fab fragment, Fab' fragment, a fragment produced by a Fab expression library, F(ab')2, Fv, disulfide linked Fv, minibody, diabody, scFv, sc(Fv)2, whole immunoglobulin molecule, small modular immunopharmaceutical (SMIP), binding-domain immunoglobulin fusion protein, camelized antibody, $V_{HH}$ containing antibody, an anti-idiotypic (anti-Id) antibody an any epitope-binding fragment(s) of any of the above. Most preferably, the antibodies are human antigen-binding antibody fragments of the present invention and include Fab, Fab' and F (ab')2, Fv, single-chain Fvs (scFv), sc(Fv)2, single-chain antibodies, disulfide-linked Fvs (sdFv) and fragments comprising either a VL or VH domain.

The antibodies according to the invention may be from any animal origin including birds and mammals. Preferably, the antibodies are human, murine (e.g. mouse and rat), donkey, monkey, rabbit, goat, guinea pig, camel, horse, or chicken antibodies.

The antibodies according to the present invention may be monospecific, bispecific, trispecific or of greater multispecificity. Multispecific antibodies may be specific for different epitopes of a target molecule, e.g. a polypeptide according to the present invention or may be specific for both a target molecule, e.g. polypeptide according to the present invention as well as for a heterologous epitope, such as a heterologous polypeptide or solid support material. Preferred are monospecific antibodies.

The term "ligand" as used herein generally refers to a substance that forms a complex with a target molecule such as a biomolecule and can thus specifically bind to the molecule with a high binding affinity. In particular, a ligand may be a signal triggering molecule capable of binding to a site on a target protein. A ligand often binds to a binding partner often referred to as a receptor. Receptor-ligand binding systems for use in the detection of target molecules are known in the art. Typically, ligand binding to a receptor alters the chemical conformation, i.e. the three dimensional shape of the receptor protein. The conformational state of a receptor protein determines the functional state of a receptor. Suitable ligands within the context of the present invention may include, for example, enzyme substrates, enzyme inhibitors, receptor agonists and antagonists, activators such as DNA-binding proteins, or neurotransmitters.

The term "lectin" as used herein refers to a protein or glycoprotein capable of specific recognition of and reversible binding to carbohydrate moieties of complex glycoconjugates without altering the covalent structure of any of the recognized glycosyl ligands. Examples of suitable lectins within the context of the present invention include monovalent lectins like bacterial and plant toxins, which are able to bind to sugar moieties in cell walls or membranes. Other suitable lectins within the meaning of the present invention are mannose binding lectins, galactose/N-acetylgalactoseamine binding lectins, N-acetylglucosamine binding lectins, N-acetylneuraminic acid binding lectins or fucose binding lectins.

The term "first binding molecule" as used herein refers to a binding molecule as described herein, capable of specifically binding to a target molecule within a sample. The first binding molecule may be attached to the particle surface by any suitable method or in any suitable manner known to the person skilled in the art via a long and rigid linker molecule as described herein.

The term "attached to the particle surface or the flat sensor surface" as used herein refers to the covalent or non-covalent binding or coupling of the first binding molecule or second binding molecule to particle surface. In particular, such a coupling may for example be a covalent binding, a van-der-Waals binding or an electrostatic binding between the layers. The attachment to the surface may be reversible or may be terminatable, e.g. by changing the pH, the temperature, the concentration of ions, by illuminating with light, by enzymatic degradation or enzymatic cleavage etc.

Figure 12:
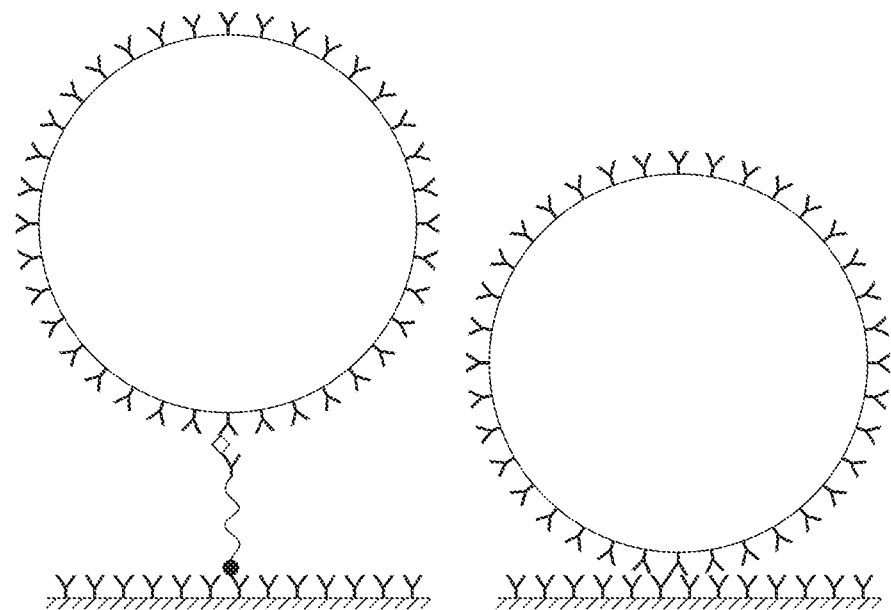
FIG. 12 shows particles bound to the surface through a specific interaction (left) or a non-specific interaction (right).

It is to be understand that either the first or second binding molecules are attached to the particle surface or flat sensor surface via a long and rigid linker molecule. This shall mean that both, the first and/or second binding molecules may be coupled to a long and rigid linker molecule as defined hereinafter. It is envisaged by the present invention to provide a certain distance between the first particle and the second particle or between the first particle and the flat sensor surface. It will be immediately appreciated by the person skilled to the art that for this purpose at least one binding molecule must be coupled to a long and rigid linker in order to provide the envisaged average extension length. For instance, if a first binding molecule is coupled to a long and rigid linker molecule, the second binding molecule may be directly attached to the surface of the second particle or the flat sensor surface. If the second binding molecule is provided with a long and rigid linker, the first binding molecule may be directly attached to the surface of the first particle. It is also conceivable that both, the first and second binding molecule are provided with a long and rigid linker in order to establish the advantageous distance. Within the context of the present invention, it is to be understood that a situation as depicted in FIG. 12 (right panel) should be avoided, where both, the first and second binding molecule are not provided with a linker structure as such an arrangement would result in only an minimal average extension length as defined herein, which would be insufficient for achieving the envisaged increase in binding kinetics.

In specific embodiments, the first binding molecule is attached to the surface of the particle via a long and rigid linker molecule. In a further specific embodiment the second binding molecule is not attached to the surface of the particle via a long and rigid linker molecule.

In specific embodiments of the present invention the coupling, binding or attachment of the first and/or second binding molecule to the particle, e.g. magnetic particle, or particle surface, or to the flat sensor surface may be a direct or indirect binding.

The term "direct binding" as used herein means that the first binding molecule has an immediate connection to the particle, e.g. magnetic particle, without the presence of intermediate, bridging or connector molecules or functionalities.

The term "indirect binding" as used herein means that the binding molecule is not directly attached to the surface of the particle, e.g. magnetic particle, but can be indirectly linked via further intermediate, bridging or connector molecules such as, for example, other binding molecules, linker molecules or charged structures. For example, avidin, streptavidin, streptavidin derivatives, (strept)avidin, avidin-related proteins, avidin-like entities such as tamavidin 1 and 2, bradavidin, NeutrAvidin etc. may be used as connector between a particle, e.g. magnetic particle, and an interacting molecule which comprises a compatible binding moiety such as biotin.

In specific embodiment, a particle, e.g. magnetic particle may be coated with or covered by an avidin or streptavidin connector. Further preferred examples of interaction couples useful as connector molecules are biotin/avidin, any antibody/antigen couple, e. g. anti FITC, FITC, anti-TexasRed/TexasRed, anti-digoxygenin/digoxygenin, and nucleic acid complementary strands as mentioned herein above. Envisaged by the present invention is in particular the use of nucleic acid complementary strands, because of the high degree of multiplexing due to the almost unlimited specific combinations. It will be also be appreciated by the person skilled in the art that such connector molecules which consist of or comprise a nucleic acid sequence can be easily integrated into a linker structure.

A "surface structure" according to the present invention can be any structure comprising molecules or a network of molecules suitable to cover a surface such as a flat sensor surface or a particle surface. The envisaged surface structure thus serves for the recognition, binding and subsequent detection of the first particles having captured a target molecule of interest.

A "flat sensor" as used herein, defines an area at which an actual sensor event occurs or is detected. Typically, the flat sensor is located at the bottom of the sample container. The flat sensor may serve for the detection of the number of bound particles, which is directly or inversely related to the amount of target molecules present in the samples. Examples of such flat sensors and corresponding sensors which may be used in the context of the present invention are provided in Bruls et al., 2009, Lab Chip, 9, 3504-3510.

The term "second binding molecule" as used herein refers to a binding molecule, which is comprised within the surface structure and which is directly or indirectly attached to the flat sensor surface as described herein or the surface of the second particle as described herein. The second binding molecule may be the same type of molecule as the first binding molecule or may be a different molecule. In preferred embodiments of the present invention first and second binding molecule molecules are the same type or class of molecules. In specific embodiments of the present invention the second binding molecule is an antibody or a fragment thereof, preferably an antibody as defined herein above. In particular preferred embodiments of the present invention the second binding protein is capable of specifically recognizing and binding to the target molecule within a sample however, at a different binding site or epitope of the target molecule than recognized by the first binding molecule. In a further preferred embodiment, the second binding molecule may be a second antibody, e.g. an antibody as defined herein above, which recognizes a first binding molecule, e.g. a first antibody, which may be an antibody as defined herein above.

The term "said first particle is capable of binding said second binding molecule of the surface directly or indirectly" as used herein shall mean that the first particle which is functionalized with a first binding molecule binds to the second binding molecule by virtue of the binding of to target molecule. In contrast, any other binding of the first particle to the surface structure, which is not mediated by the target molecule as defined herein is considered to be a non-specific binding.

"Directly binding" in this context thus means that the first binding molecule, which acts as a capture molecule, recognizes and binds the target molecule thereby forming a capture complex, and which in turn is bound and recognized by the second binding molecule of the surface structure. In this regard "indirectly binding" means that the first particle is bound to via one or several capture complexes to the second binding molecule. It is also conceivable that several target molecule-binding molecule aggregates or complexes mediate the indirect binding of the first particle to the second binding molecule of the surface structure, while the binding is still considered as being specific since it is mediated by the target molecule.

The term "linker molecule" as described herein can be any structure suitable to provide the attachment of the first binding molecule and/or the second binding molecule to the surface. The skilled person would be aware of means and methods for coupling a linker molecule to a particle surface or a flat sensor surface. According to a further specific embodiment of the present invention, the increased end to end distance required for an enhanced binding kinetics as described herein can be achieved by providing the surface structure of the flat sensor surface with a linker molecule having a sufficient long average extension.

For this purpose the surface and/or the linker molecule may comprise an anchoring moiety capable of coupling a linker to a surface. The "anchoring moiety" as used herein is to be understood as a connector in between a linker molecule as defined herein and the surface or one or more surface molecules directly on the particle surface. Of particular relevance is thus any bridging or connector molecule as described herein. For example, avidin, streptavidin derivatives, (strept)avidin, avidin-related proteins, avidin-like entities such as tamavidin 1 and 2, bradavidin, NeutrAvidin etc. may be used for anchoring of a linker molecule and a surface or surface structure as described herein. For instance, the anchoring moiety may comprise biotin, while the surface is coated or functionalized with streptavidin. Means and methods for coating a surface with streptavidin are known to the skilled person or can be derived from suitable textbooks or literature sources.

Further preferred examples of interaction couples suitable as connector molecules for anchoring are biotin/avidin, any antibody/antigen couple, e.g. anti FITC, FITC, anti-Texas-Red/TexasRed, anti-digoxygnenin/digoxygenin, nucleic acid complementary strands as mentioned herein above. The anchoring moiety may also comprise nucleic acid complementary strands, because of the high degree of multiplexing due to the almost unlimited specific combinations. It will be also appreciated by the person skilled in the art that such connector molecules, which consist of a nucleic acid sequence can be easily integrated into a linker structure.

Also envisaged by the present invention are anchoring moieties comprising or consisting of a chemical group which may be covalently linked (e.g. cross-linked) by coupling chemistry to a surface or a molecule bound to a surface. Crosslinking is the process of chemically joining two or more molecules by a covalent bond often referred to as bioconjugation. Typically, crosslinking reagents (or crosslinkers) are molecules that contain two or more reactive ends capable or chemically attaching to specific functional groups on proteins or other molecules such as protein functional groups, e.g. primary amine (—NH2), carboxyls (—COOH), sulfhydryls, or carbonyls (—CHO), or crosslinker reactive groups such as carbodiimide (e.g., EDC), NHS ester, imidoester, PFP ester, hydroxymethyl phosphine, maleimide, haloacetyl (bromo- or iodo-), pyridyldisulfide, vinyl sulfone, hydrazide, diazirine, aryl azide, or isocyanate.

Also envisaged by the present invention is that the linker molecule has a certain length so as to act as a spacer molecule, i.e. to provide a certain distance of the binding molecule and the particle surface. It is understood that the provision of such a distance may provide several other advantages:

For instance, a certain distance may result in less unspecific binding of the particles to other molecules and to each other. Moreover, non-specific clustering of the particles, e.g. magnetic particles, which usually occur may be minimized.

Linker molecules according to the present invention thus may have the function of a connector molecule and/or the function of a spacer. For this purpose, these polymeric molecules preferably have a certain length, strength, and/or rigidity in order to be able to act like polymeric fibers.

Also envisaged by the present invention is the use of polymers that assemble in fibers, e.g. by dimerization or higher order multimerization. The envisaged advantage is that rigidity as defined herein may be increased. Also envisaged is the use of "assisting molecules" which help to establish a higher order structure having the envisaged rigidity, which in turn results in the envisaged average extension length of the linker. One envisaged example is a single stranded nucleic acid molecule, which may assemble in to a dimeric helix structure, and which in turn may assemble with an assisting molecule. Other envisaged examples for assisting molecules are proteins capable of binding nucleic acids such as to ssDNA, dsDNA or both (e.g. DNA binding proteins) or to ssRNA, dsRNA or both (e.g. RNA-binding proteins). The binding of such factors or proteins may preferably be guided by specific binding motifs recognized by the binding protein, which may be present in the nucleic acid molecule, e.g. the dsDNA or ssDNA or ssRNA. Once such binding factors are bound on the nucleic acid molecule, the rigidity of the linker may be enhanced and lead to linkers with increased average extension length. Such a linker modification may be carried out before or during an assay. In further specific embodiments of the present invention, assisting molecules such as RNA or DNA binding proteins may comprise protein-protein interaction domains, e.g. SH3, PDZ, 14-3-3, SH2 domains or any other suitable domain known to the person skilled in the art. Secondary binding factors, which comprise compatible recognition domains or interaction domains, may accordingly be provided allowing the assembly of complexes comprising nucleic acids bounds by assisting molecules, which in turn may be bound by secondary interacting molecules. In further embodiments, rigid linker structures may be provided in the form of polymeric polypeptides, e.g. based on the form and/or molecular identity of collagen, or collagen-like proteins such as Scl1, Scl2, SclA, or SclC. These molecules may further be combined with other linker molecules or functional groups as defined herein.

In further specific embodiments of the present invention, the polymeric linker molecules may be polymeric molecules capable of self-assembly under suitable conditions. Accordingly, the polymeric molecules may be provided in conjunction with particles leading to the assembly of the polymers on the surface of the particle. The self-assembly may be controlled by suitable parameters, e.g. the concentration of monomers or polymeric units necessary for the polymerization, the concentration of bridging factors for monomers or polymeric units, the pH of the reaction environment, the temperature, the presence of ions, the presence of assisting factors such as proteins, etc. The self-assembled polymers may, in further embodiments, be disintegrated upon the change of such a suitable condition, e.g. by the change of pH, the reduction or increase of the concentration of factors or monomers, the change of temperature etc.

It is also conceivable that the linker molecule comprises or consists of a charged structure as defined herein or be integrated in a steric surface structure as described herein.

In further specific embodiments of the present invention, the linker molecules may be linear, circular, or branched-like molecules, or a mixture thereof.

Suitable linker molecules within the context of the present invention may be, for example, nucleic acids, ribonucleic acids, peptides, polypeptides, proteins, carbohydrates, lipids, polyethylene glycol, polysaccharides, dendrimers, dendrons, nanotubes, or any suitable derivatives or combinations thereof.

Nucleic acid molecules as defined herein above may advantageously also be used as "nucleic acid linker molecules". These linker molecules may comprise single and/or double stranded nucleic acid molecules, preferably DNA molecules, or any type of derivative thereof. The DNA may, for example, be in the form of, e.g. A-DNA, B-DNA or Z-DNA or any mixture of these forms. The linker molecule may also be a PNA, CNA, HNA, LNA or ANA molecule, or any mixture or combination thereof, or any mixture or combination with other linker molecule as defined herein, e.g. with a any type of nucleic acid such as DNA or RNA.

The term "PNA" relates to a peptide nucleic acid, i.e. an artificially synthesized polymer similar to DNA or RNA which is used in biological research and medical treatments, but which is not known to occur naturally. The PNA backbone is typically composed of repeating N-(2-aminoethyl)-glycine units linked by peptide bonds. The various purine and pyrimidine bases are linked to the backbone by methylene carbonyl bonds. PNAs are generally depicted like peptides, with the N-terminus at the first (left) position and the C-terminus at the right. While DNA and RNA have a desoxyribose and ribose sugar backbone, respectively, the PNA-backbone is composed of repeating N-(2-aminoethyl)-glycine units linked by peptide bonds. It is known in the art that PNA oligomers also show greater specificity in binding to complementary DNAs. Further details may be derived from any suitable literature source or textbook, e.g. Nielsen P E, Egholm M (1999), An Introduction to Peptide Nucleic Acid, Curr. Issues Mol. Biol. 1 (2): 89-104.

The term "CNA" relates to an aminocyclohexylethane acid nucleic acid. Furthermore, the term relates to a cyclopentane nucleic acid, i.e. a nucleic acid molecule comprising for example 2'-deoxycarbaguanosine.

The term "HNA" relates to hexitol nucleic acids, i.e. DNA analogues which are built up from standard nucleobases and a phosphorylated 1,5-anhydrohexitol backbone.

The term "LNA" relates to locked nucleic acids. Typically, a locked nucleic acid is a modified and thus inaccessible RNA nucleotide. The ribose moiety of an LNA nucleotide may be modified with an extra bridge connecting the 2' and 4' carbons. Such a bridge locks the ribose in a 3'-endo structural conformation. The locked ribose conformation enhances base stacking and backbone pre-organization. This may significantly increase the thermal stability, i.e. melting temperature of the oligonucleotide.

The term "ANA" relates to arabinoic nucleic acids or derivatives thereof. A preferred ANA derivative in the context of the present invention is a 2'-deoxy-2'-fluoro-beta-D-arabinonucleoside (2'F-ANA).

In certain embodiments of the present invention a nucleic acid linker molecule may be present in a double-stranded or duplex form, i.e. comprising a strand and a complementary or anti-parallel counter-strand of a nucleic acid molecule associated by base pairing between the strands, or a sense or antisense-strand of a nucleic acid molecule. The term "sense strand" as used herein refers to a molecule comprising the sequence, which is the same as that of a messenger RNA copy that is or may be translated into a protein. The term, within the context of the present invention, additionally refers to molecules comprising one strand of a duplex nucleic acid molecule, which is not identical to its complementary counter-strand. Accordingly, the term "anti-sense strand" as used herein refers to the molecule comprising the complementary or opposite strand with respect to the sense strand as defined above. In further specific embodiments, a nucleic acid linker molecule may be a double stranded or duplex ribonucleic acid molecule. Alternatively, the nucleic acid linker molecule may comprises a single-stranded nucleic acid or a single stranded ribonucleic acid molecule.

In specific embodiments, the linker molecule is a ribonucleic acid molecule, or any mixture of a ribonucleic acid with any of the other mentioned nucleic acid molecules or with any other linker molecule as defined herein, preferably an RNA molecule, or any type of derivative thereof. The RNA may be in the form of, e.g. p-RNA, i.e. pyranosysl-RNA or structurally modified forms like hairpin RNA or a stem-loop RNA.

The nucleic acid, including ribonucleic acid molecules, may be of different base compositions and/or lengths as defined herein. The length of the linker molecule may be made dependent on the size or diameter of the particle, the presence, size or length of charged structure molecules as defined herein, the envisaged overall specific net charge of the particle, in particular since nucleic acid molecules if used as linkers may provide a specific net charge to the particle, any envisaged end-to-end-distance between binding molecule and particle surface, or any envisaged flexibility, rigidity or stability of the linker molecule. In certain embodiments of the present invention, the nucleic acid linker molecule may be a charged or un-charged molecule. The term "un-charged nucleic acid linker molecule" as used herein relates to a net charge of the molecule of about 0.

In a particular preferred embodiment of the present invention the linker molecule is or comprises a molecule selected from the group consisting of a double stranded or dsDNA, double stranded or dsRNA, PNA, a PNA-DNA duplex, and a RNA-DNA duplex.

One advantageous aspect, which is also envisaged by further preferred embodiments of the present invention, is that PNAs and PNA/DNA or PNA/DNA duplexes are not easily recognized by either nuclease or proteases making them resistant to enzymatic degradation.

In further embodiments of the present invention, suitable nucleic acids may also comprise or consist of single stranded DNA molecules of different base compositions and/or lengths. The single stranded molecules may, for example, encompass the repetition of base sequence, be entirely random, or be derived from nature, or be of only one base, e.g. AAA etc., TTT etc., CCC etc., or GGG etc.; or comprise stretches of such monobase regions, e.g. be comprised only of A and C, or C and T.

Peptides, polypeptides or proteins may be suitable linkers due to their form, rigidity and confirmation. Peptide molecule linkers may be of different amino acid compositions and/or lengths. The length of a peptide molecule linker may vary between about 3 amino acids to about 35 amino acids. Also envisaged are other lengths or any length value within the indicated range. The peptide linker molecule may, for example, have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acids. The amino acid composition may vary between mono amino acid compositions, e.g. only one of the naturally produced amino acids or any derivative thereof or of synthetically available amino acids, and completely random amino acid compositions comprising or be selected from all known amino acids. Also envisaged are compositions comprising 2, 3, 4, 5, 6, 7, 8, 9, 10, 11, 12, 13, 14, or 15 or more different amino acids. The amino acids may be present in stretches of identical amino acids or be provided in the form of pattern or motifs, or be randomly distributed.

The length of the peptide molecules linker molecule may in specific embodiments be made dependent on the size or diameter of the particle, the presence, size or length of charged structure molecules as defined herein the envisaged overall specific net charge of the particle, in particular since peptide molecules if used as linkers may provide a specific net charge to the particle, any envisaged end-to-end-distance between binding molecule and particle surface, or any envisaged flexibility, rigidity or stability of the linker molecule. In certain embodiments of the present invention, the peptide linker molecule may be a charged or un-charged molecule. The term "un-charged peptide linker molecule" as used herein relates to a net charge of the molecule of about 0.

Protein or polypeptide linker molecules may be of different amino acid compositions and/or lengths. The length of the protein or polypeptide molecule may vary between about 35 amino acids to about 500 amino acids, or more. Also envisaged are other lengths or any length value within the indicated range. The peptide molecule may, for example, have a length of 35, 40, 50, 60, 70, 80, 90, 100, 120, 130, 140, 150, 200, 250, 300, 350, 400, 450, or 500 amino acids or more.

The length of the protein or polypeptide linker molecule may in specific embodiments be made dependent on the size or diameter of the particle, the presence, size or length of charged structure molecules as defined herein above, the envisaged overall specific net charge of the particle, in particular since protein or polypeptide molecules if used as linkers may provide a specific net charge to the particle, any envisaged end-to-end-distance between binding molecule and particle surface, or any envisaged flexibility, rigidity or stability of the linker molecule. In certain embodiments of the present invention, the polypeptide or protein linker molecule may be a charged or un-charged molecule. The term "un-charged polypeptide or protein molecule" as used herein relates to a net charge of the molecule of about 0.

"Carbohydrate molecules" may be suitable linkers due to their form, rigidity and confirmation. Such carbohydrates may be of different compositions and/or lengths. The length of the molecule may vary between about 5 C atoms to about 100 C atoms, or more. Also envisaged are other lengths or any length value within the indicated range. The carbohydrate molecule may, for example, have a length of 5, 6, 7, 8, 9, 10, 15, 20, 25, 30, 35, 40, 45, 50, 55, 60, 65, 70, 75, 80, 85, 90, 95 or 100 C atoms or any other number of C atoms between the indicated values.

The length of the carbohydrate linker molecule may in specific embodiments be made dependent on the size or diameter of the particle, the presence, size or length of charged structure molecules as defined herein, the envisaged overall specific net charge of the particle, in particular since carbohydrate molecule if used as linkers may provide a specific net charge to the particle, any envisaged end-to-end-distance between binding molecule and particle surface, or any envisaged flexibility, rigidity or stability of the linker molecule. In certain embodiments of the present invention, the carbohydrate linker molecule may be a charged or un-charged molecule. The term "un-charged carbohydrate molecule" as used herein relates to a net charge of the molecule of about 0.

"Lipids" may be suitable linker molecules due to their form, rigidity and confirmation. Lipids constitute a broad group of naturally occurring molecules including, but not limited to, fats, waxes, styrols, fat-soluble vitamins (such as vitamins A, D, E and K), monoglycerides, digycerides, phospholipids. Such lipids are typically built of a lipid tail and a headgroup. Examples of suitable lipids include phospholipids, e.g. phosphatidyl ethanolamine, phosphatidylcholine, egg phosphatidyl-ethanolamine, dioleoylphosphatidyl ethanolamine. Particularly preferred are the phospholipids MPPC, DPPC, DPPE-PEG2000 or Liss Rhod PE. The lipids may be of different compositions and/or lengths. The length of the molecule may vary between about 5 C atoms to about 100 C atoms, or more. Also envisaged are other lengths or any length value within the indicated range. The lipid molecule may, for example, have a length of about 5, 6, 7, 8, 9, 10, 15, 20, 25, 30, 35, 40, 45, 50, 55, 60, 65, 70, 75, 80, 85, 90, 95 or 100 C atoms or any other number of C atoms between the indicated values.

The length of the lipid linker molecule may in specific embodiments be made dependent on the size or diameter of the particle, the presence, size or length of charged structure molecules as defined herein, the envisaged overall specific net charge of the particle, in particular since lipid molecules if used as linkers may provide a specific net charge to the particle, any envisaged end-to-end-distance between binding molecule and particle surface, or any envisaged flexibility, rigidity or stability of the linker molecule. In certain embodiments of the present invention, the lipid spacer molecule may be a charged or un-charged molecule. The term "un-charged lipid molecule" as used herein relates to a net charge of the molecule of about 0.

In further preferred embodiment, the linker structure may also comprise or consist of a non-biological polymer. The term "non-biological polymer" as used herein refers to a polymer which is not from a biological source (biopolymer) and is chemically synthesized. Suitable polymers for this purpose have been described in the art (e.g. by Ratner, B. D.; Hoffman, A. S.; Schoen, F. J.; Lemons, J. E., Biomaterials Science, 2nd Ed.; Eds.; Elsevier: London, 2004). Examples of a suitable non-biological polymers are biologically-degradabele polymers such as poly(glycolic acid) (PGA) or poly(lactic acid) (PLA), poly(caprolactone) (PCL, poly(N-vinyl-2-pyrrolidone) (PVP), polydioxanone (PDS), or poly (ethylene glycol) (PEG) or copolymers thereof also termed hetereopolmers that are derived from two (or more) monomeric species. The term "block polymer" as used herein refers to copolymers comprising two or more homopolymer subunits linked by covalent bonds. Block copolymers with two or three distinct blocks are called diblock copolymers and triblock copolymers, respectively. Preferred block copolymers include, but are not limited to poly(lactide-co-glycolide) copolymers (PLGA), poly(ethylene oxide)-poly(propylene oxide) (PEP-PPO) poly(ethylene oxide)-poly (propylene oxide) poly(ethylene oxide) (PEP-PPO-PEO), poly(ethylene oxide)-block-poly(L-lactide) (PEG-PLLA), poly(ethylene oxide)-block-poly(caprolactone) (PEG-PCL), poly(ethylene glycol)-block-poly($\alpha$-hydroxy acid) (PEG-PHA) or Pluronic P-105.

Polyethylene glycol molecules may in particular be used as "polyethylene glycol linker molecules" in the context of the present invention due their form, potential rigidity and confirmation. Polyethylene glycols envisaged by the present invention may be of different compositions and/or lengths.

Preferred polyethylene glycol (PEG) variants include polydispers or monodisperse PEG molecules. Particularly preferred is monodisperse PEG. PEGs may further be branched, e.g. having 3-10 PGE chains emanating from a central core group, be star PEGs having 10 to 100 PEG chains emanating from a central core group, or be comb PEGs which have multiple PEG chains grafted to a different polymer or linear PEG backbone. According to the PEG's average molecular weights, envisaged PEGs may be PEG 10,000, PEG 12,000, PEG 15,000, PEG 20,000 or PEGs having higher molecular weights. Particularly preferred is a PEG larger than PEG 10,000.

Smaller PEG molecules such as, for example, PEG 400, PEG 600, PEG 800, PEG 1000, PEG 1500, PEG 2000, PEG 3350, PEG 4000, PEG 6000, or PEG 8000 may also be used as part of linker structures, e.g. in combination with one or more linker molecules as defined herein.

The length of the polyethylene glycol linker molecules may in specific embodiments be made dependent on the size or diameter of the particle, the presence, size or length of charged structure molecules as defined herein, or the envisaged overall specific net charge of the particle, in particular if polyethylene glycol molecule derivatives which carry electrical charges are used, or any envisaged end-to-end-distance between binding molecule and particle surface, or any envisaged flexibility, rigidity or stability of the linker molecule. In certain embodiments of the present invention, the polyethylene glycol linker molecule, in particular a derivative thereof or modified version thereof, may be a charged or un-charged molecule. The term "un-charged polyethylene glycol molecule" as used herein relates to a net charge of the molecule of about 0.

"Dendrimers" or "dendrimetic linker molecules" may be any repeatedly branched, roughly spherical large molecules. Such dendrimers may be of different compositions and/or lengths, and/or degree of branching. The length may be made dependent on the envisaged overall specific net charge, the envisaged end-to-end-distance between binding molecule and particle surface, the envisaged flexibility, rigidity or stability of the linker molecule, and/or the envisaged number of charged molecules per particle. Dendrimers as envisaged by the present invention may comprise low-molecular weight or high-molecular weight species. The dendrimers according to the present invention are preferably un-charged, i.e. the molecules show a net charge of 0.

Also envisaged by the present invention is the use of dendrimers according to the present invention as a part of a linker. For this purpose the dendrimers may, in certain embodiments, comprise functional groups on the molecular surface, e.g. hydrophilic groups, or alternatively have internal functionality. Dendrimers as envisaged for the purposes of the present invention may be dendrimers of $1^{st}$, $2^{nd}$, $3^{rd}$, $4^{th}$, or a higher generation. Preferred dendrimers include, for example, newkome dendrimer or arbolol, and Polyamidoamine (PAMAM). It will be appreciated by one of skill in the art that dendrimers lead to structures that can be advantageously used to provide a voluminous and steric surface structure on the particle surface or flat surface wherein the linker molecule as described herein above is a part of such are structure or is embedded therein. Further variants to be used within the context of the present invention, as well as synthesis methods etc. would be known to the person skilled in the art or can be derived from suitable documents, such as "Dendrimers and other dendritic polymers", Frechet and Tomalia, J. Wiley.

"Dendrons" or "dendronic linker molecules" are understood as containing a single chemically addressable groups of dendrimers, i.e. a focal point of a dendrimer as defined herein above. The dendrons according to the present invention are preferably un-charged, i.e. the molecules show a net charge of 0. In particular embodiments of the present invention, dendrons may be used as a part of a linker as defined herein.

The term "nanotube" as used herein refers to carbon nanotubes, i.e. allotropes of carbon with a cylindrical nanostructure. Such nanotubes may be single walled nanotubes or multi walled nanotubes. The present invention also envisages linker molecules of the fullerene structural family of different types, forms and complexity, e.g. spherical, or ellipsoid buckyball forms, buckyball fullerene, or a combination of nanotubes with backbyballs etc. The nantotubes according to the present invention or other linker suitable linker molecules known to the person skilled in the art are preferably un-charged, i.e. the molecules show a net charge of 0.

Figure 4:
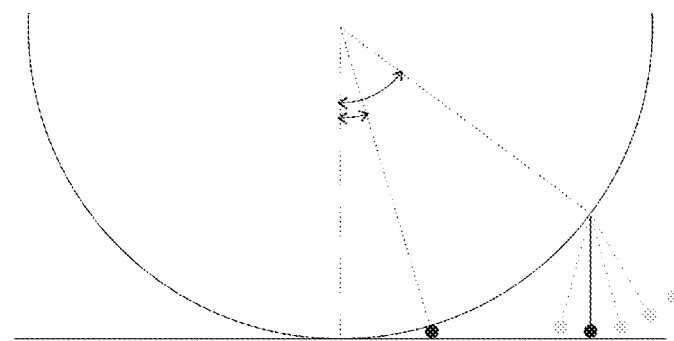
FIG. 4 illustrates the increased number of orientations in which a particle can bind to the surface if the attachment point (represented by the small black circle) is extended further from the particle.

The linker molecule according to the present invention preferably has certain length and consistency in order to be able to increase the binding probability of the particle to a surface to result in improved binding kinetics. In the prior art linker or spacers have merely been considered for the connection of a binding molecule to surfaces and in terms of accessibility of the binding molecules. However, the length of a linker, especially with respect to a maximal extension from the particle, was not described previously. Envisaged by the present application is therefore to provide suitable linker molecules having a certain length which are suitable for extending the attachment point of the binging molecule as defined herein further away from the from the particle surface or the flat sensor surface. As can be seen in FIG. 4, the envisaged approach opens up an increased number of orientations in which a particle can bind to the surface.

Figure 6:
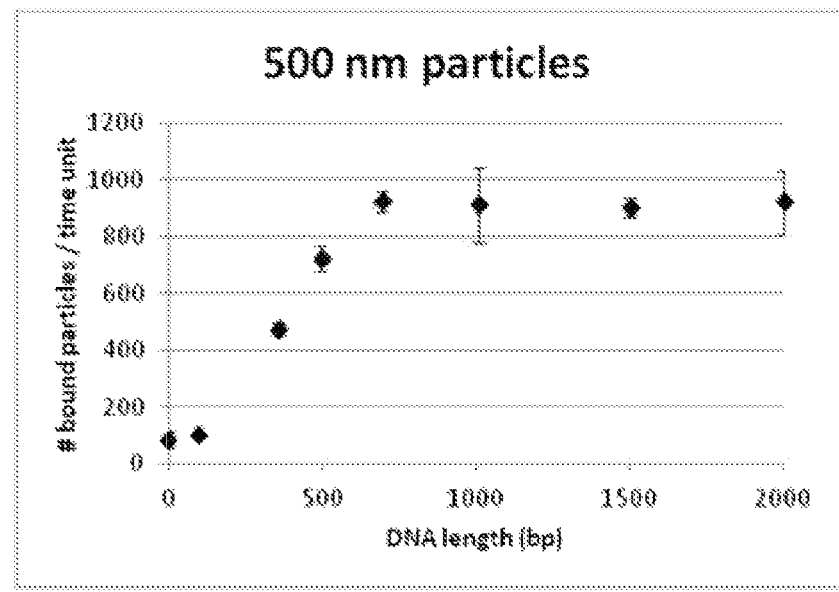
FIG. 6 depicts a graph showing the number of particles bound as a function of DNA linker length. 500 nm streptavidin-coated particles were incubated with dsDNA of varying length. Each DNA molecule contained one biotin moiety at one end of the DNA molecule, a Texas Red molecule at the other end of the molecule. The solution containing particles and DNA were injected into a cartridge and bound to the sensor surface, coated with anti Texas Red antibodies using magnetic attraction. By repeatedly registering the number of particles that had bound to the surface after a short magnetic wash step that removed non-bound particles from the surface, the binding rate (expressed in number of bound particles per time unit) was determined.
Figure 7:
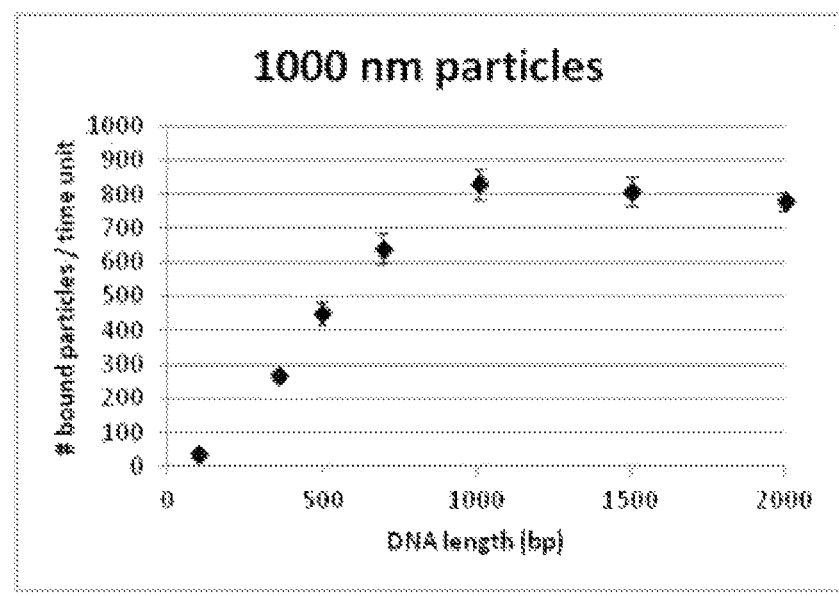
FIG. 7 depicts a graph showing the number of particles bound as a function of DNA linker length. Details are similar as for FIG. 6, however particles with 1000 nm diameter were used.

Also envisaged by the present invention is thus a particle as defined herein where the capture or binding molecule is attached to the particle surface via a linker molecule having a certain average extension length as defined herein. In a specific example of the present invention, the use of a long and rigid dsDNA molecule as a linker results in significant average extension of the binding molecule from the surface. The envisaged approach results in a significant enhancement of the kinetics of binding a particle to the flat sensor or particle surface as defined herein. As can be derived from FIGS. 6 and 7, it could be demonstrated that the number of bound particles is a function of the linker length. In these examples, 500 nm and 1000 nm streptavidin-coated particles were incubated with dsDNA linker of varying length. Each dsDNA linker molecule contained one biotin molecule at one and a Texas Red molecule at the other end and the flat sensor surface was coated with anti Texas Red antibodies. The graphs according to FIGS. 6 and 7 show the increase of the number of bound particles with increasing length (bp) of the dsDNA linker molecule. The optimal length of larger than 700 bp for 500 nm particles corresponds to a contour length of more than 240 nm and an average extension length of more than 140 nm. As can be seen in FIG. 7, the optimum linker length is 1000 bp corresponding to a contour length of 340 nm for a larger particle (e.g. 1000 nm) and an average extension length of about 170 nm. The optimal linker length is thus dependent on the particle size and may, in certain embodiments of the present invention, be adapted to the particle size or particle diameter, e.g. on the basis of the experimental results described in the Examples portion herein below.

The term "average extension length" as used herein is defined as the root mean square end-to-end distance of the linker $\sqrt{<R^2>}$, which can be described according to the worm-like chain model as:

$$<R^2>=2Pl[1-(P/l)(1-e^{-l/P})],$$

wherein P is the persistence length of the polymer and l is the contour length of the linker.

The term "contour length" as used herein refers to the contour length of a polymer chain as the length at maximum physically possible extension.

Several biologically important polymers can be effectively modeled as worm-like chains, including double-stranded DNA and RNA, unstructured RNA and unstructured polypeptides. The Kratky-Porod-worm-like-chain-model is suitable for modeling of semi-flexible polymers in order to approximate end-to-end distances and persistence lengths. The skilled person is however aware of numerous other theoretical models, e.g. as described hereinafter, to approximate end-to-end distance and persistence lengths.

The term "persistence length, P" as used herein refers to a basic mechanical property quantifying the stiffness or rigidity of a polymer or a string and is defined as the length over which correlations in the direction of the tangent are lost. In chemistry, it can also be defined as the average sum of the projections of all bonds j≥i on bond i in an indefinitely long chain (Flory, Paul J. (1969), Statistical Mechanics of Chain Molecules, New York: Interscience Publishers). When the angle θ between a vector that is tangent to the polymer at position 0 (zero) and a tangent vector at a distance L away from position 0, the expectation value of the cosine of the angle falls off exponentially with distance, $$<\cos \theta>=e^{-(L/P)}$$

where P is the persistence length and the angled brackets denote the average over all starting positions. Flexible polymers such as PEG can be described using the Flory model (random walk).

The persistence length can be also defined using the bending stiffness $B_s$, the Young's modulus E and the section of the polymer chain as described in Mofrad, M. R. K, "Cytoskeletal mechanics: models and measurements", Cambridge Univ Press, 2006.

$$p_l = \frac{B_s}{k_B T}$$

$$B_s = EI$$

In the case of a rigid and uniform rod I can be expressed as:

$$I = \frac{\pi a^4}{4}$$

where α is the radius.

In polymer science, persistence length can be also defined as one half of the Kuhn length, i.e. the length of hypothetical segments that the chain can be considered as freely joined. The persistence length equals the average projection of the end-to-end-vector on the tangent to the chain contour at a chain end in the limit of infinite chain length.

Figure 5:
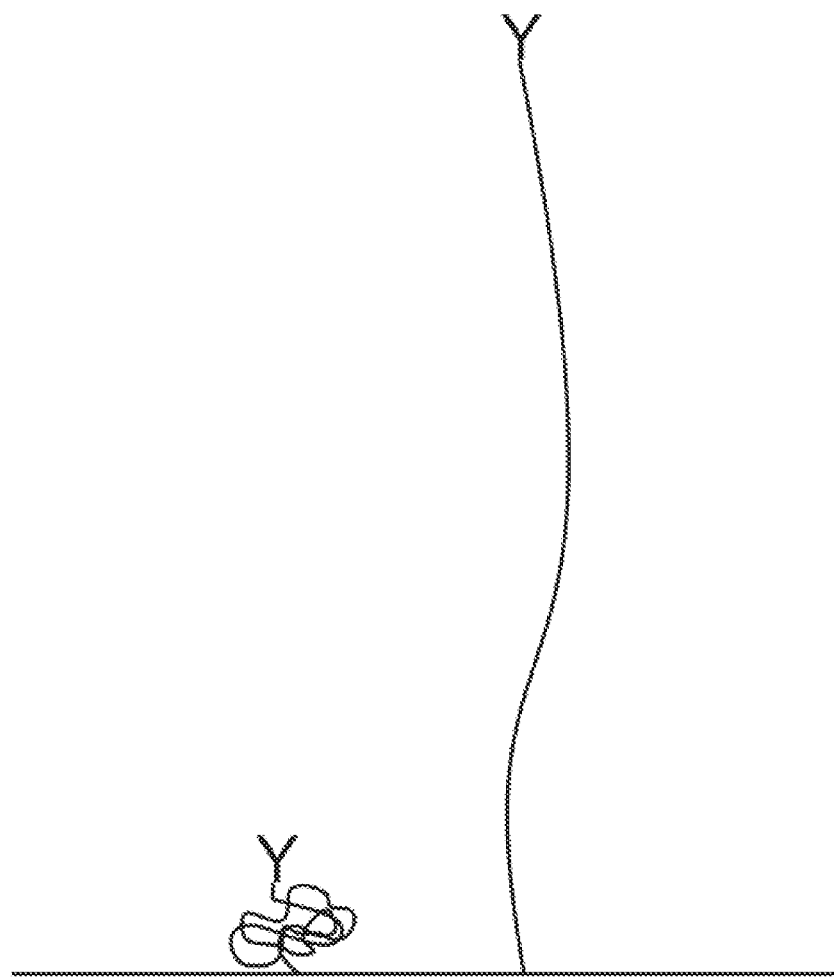
FIG. 5 shows a sketch comparing the extension of an antibody attached to the surface via a PEG linker (left) or dsDNA linker (right), both with the same contour length.

As can be seen in FIG. 5, the length of a linker molecule per se is not a sufficient criterion in order generate a high end-to-distance, i.e. to position the binding molecule away from the particle surface or flat sensor surface. FIG. 5 exemplary shows a sketch comparing the extension of an antibody attached to the surface via a PEG linker (left) versus a dsDNA linker (right) both having the same contour length. The use of molecules or polymers which are very long in terms of contour length but also flexible may however result in a fold up of the molecule and finally a globular structure with a minor extension. Envisaged is thus an enhanced extension of the binding molecule from the surface or an increased end-to-end distance that can be achieved by the provision of a long as well as rigid linker as described herein. In the example as illustrated in FIG. 5, the average extension length of a 170 nm dsDNA molecule, which is considered as rigid as defined herein, is 10 fold larger than the average extension length of a PEG molecule of the same contour length. It is however conceivable to use also very flexible linkers with a large contour length provided that the resulting average extension is sufficient large to provide the envisaged effect.

Envisaged by the present application is also to provide suitable conditions under which the average extension length as defined herein is increased in order to result in enhanced binding kinetics. In particularly preferred embodiments of the present invention examples for suitable long and rigid linker is are double stranded nucleic acid-based molecules. For example, due to the high rigidity a 700 bp dsDNA linker $\sqrt{<R^2>}$ would be equal ~140 nm, a 1000 bp linker would result in $\sqrt{<R^2>}$ of around ~170 nm.

In specific embodiments of the present invention, the linker molecules may have an average extension length of at least about 60 nm, preferably up to about 500 nm, preferably of at least about 65 nm, 70 nm, 75 nm, 80 nm, 85 nm, 90 nm 95 nm or 100 nm, even more preferably of at least about 110 nm, 120 nm, 130 nm, 140 nm, 150 nm, 160 nm, 170 nm, 180 nm, 190 nm, or 200 nm, even more preferably of at least about 220 nm, 250 nm, 270 nm, or 300 nm, most preferably of at least 320 nm, 350 nm, 370 nm, or 400 nm. In further embodiments, the average extension length of the linker molecule may also be larger than 400 nm. The linker molecule may also have any other suitable average extension length in between the indicated values.

In specific embodiments of the present invention the optimal average extension length of the linker molecule is at least ⅒, preferably at least ⅙, preferably ⅛, more preferably at least ¼, and most preferably ⅔ of the diameter of a particle as described herein.

In a further preferred embodiment, the average extension length is at least 10%, 11%, 12%, 13%, 14%, 15%, 16%, 17%, 18%, or 19%, more preferably 20%, 21%, 22%, 23%, 24%, 25%, 26%, 27%, 28%, or 29%, even more preferably 30%, 31%, 32%, 34%, 35%, 36% 37%, 38%, 39%, most preferably 40%, 41%, 42%, 43%, 44%, 45%, 46%, 47%, 48%, 49%, or 50% of the diameter of a particle as described herein.

In particularly preferred embodiments a particle of a diameter of about 500 nm may comprise linker molecules showing an average extension length of about 25 to 30%, more preferably of about 27% of the particle diameter. In further preferred embodiments a particle of a diameter of about 1000 nm may comprise linker molecules showing an average extension length of about 15 to 20%, more preferably of about 17% of the particle diameter.

Also envisaged by the present invention is the provision of detection conditions or changes in detection conditions such as a pH shift or a temperature shift leading to a conformational change of the linker molecule and/or a change in the rigidity characteristics of the linker molecule.

For instance, a linker molecule with a high contour length but low rigidity that is folded up could be extended by the envisaged approach. It is also conceivable to add a further compound, composition, molecule, solvent, and/or ion that may interact or react with the linker molecule so as to result in an increased rigidity of the linker molecule and to an enhanced average extension of the linker molecule as defined herein above.

Figure 8:
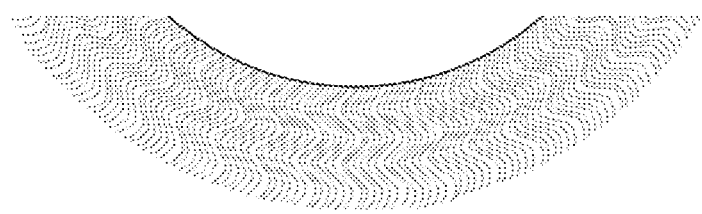
FIG. 8 shows particle with a high surface density of linker molecules. Although the linker molecules are relatively stretched, the high steric hindrance will decrease linker mobility.

It is also conceivable to force an increased extension by virtue of increasing the surface density of the linker molecule. It is appreciated that although the average extension length of flexible polymers is decreased due to the formation of globular structures, an increase of the density of the linker molecule on the particle or flat sensor surface may result in an overlap of molecules so that the linker molecules may stabilize each other as can be seen in FIG. 8. The results shown in FIG. 9 however demonstrate that flexibility of the linker is an important aspect contributing to an enhanced binding kinetics. The charts in FIG. 9 demonstrate that the binding kinetics are decreased as a result of decreased mobility upon overloading the surface with more dsDNA molecules. Envisaged is thus a long and rigid linker molecule that may still retain a certain mobility sufficient to perform the different orientations of the linker molecule in order to arrive at the envisaged increase of binding kinetics. The number and/or length of linker molecules may accordingly be adapted to the particle properties, in particular the particle size.

As used herein "rigidity" or "rigid" also termed as "stiffness" define the property of a solid body to resist deformation. It is appreciated that rigidity of a linker molecule essentially contributes to the average extension length. "Flexible" as used herein thus refers to the property of a solid body, which can be easily deformed. In the context of the present invention, a flexible molecule, polymer, or linker thus has a low rigidity as defined herein which may result in a bending and fold up of the molecule.

In a specific embodiment of the present invention the rigidity of a linker molecule is determined via the root mean square end-to end distance of the linker $\sqrt{<R^2>}$ as defined above. In certain embodiments, the rigidity may accordingly be measured in terms of the linker's root means square end-to-end distance or average extension length in comparison to its contour length as defined herein. Thus, for example, a contour length of a linker molecule, which is essentially identical to the average extension length of a linker molecule indicates a high rigidity of the linker molecule. On the other hand, a contour length of a linker molecule, which is significantly larger than the average extension length of said linker indicates a low rigidity of the linker molecule.

In preferred embodiments of the present invention, the rigidity and length of the linker molecule is selected such that the root mean square end-to end distance of the linker $\sqrt{<R^2>}$ is at least about 5%, 10%, or 15%, preferably about 20%, 25%, or 30%, 35%, even more preferably about 40%, 45%, or 50%, most preferably about 55%, 60%, 65%, 70% or 75% with respect to the particle diameter.

In another preferred embodiment of the present invention the rigidity and length of said linker molecule is selected such that root mean square end-to end distance of the linker $\sqrt{<R^2>}$ is at least about 10%, 11%, 12%, 13%, 14%, 15%, 16%, 17%, 18%, or 19%, more preferably 20%, 21%, 22%, 23%, 24%, 25%, 26%, 27%, 28%, or 29%, even more preferably 30%, 31%, 32%, 34%, 35%, 36% 37%, 38%, 39%, most preferably 40%, 41%, 42%, 43%, 44%, 45%, 46%, 47%, 48%, 49%, or 50% with respect to the particle diameter.

In particularly preferred embodiments of the present invention, a higher increase of sensitivity and binding kinetics can be achieved when both of surface structures, namely the surface of the particle and the flat sensor surface comprise a long and rigid linker as described herein above.

Figure 10:
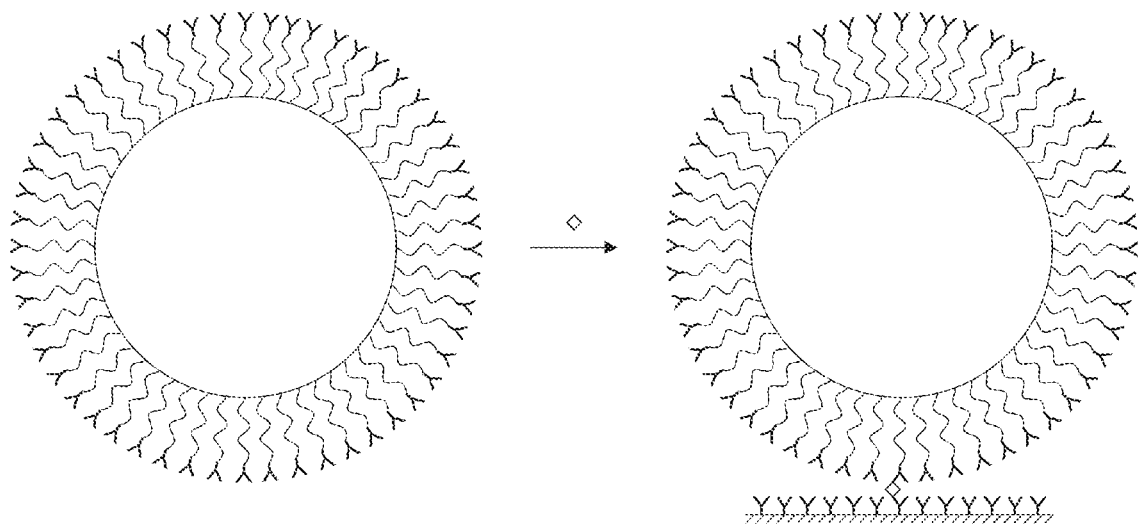
FIG. 10 shows a particle, pre-loaded with capture molecules attached to the surface via a long, rigid linker During the assay, the target molecule (diamond) is bound to the particle and subsequently to the surface.

Also envisaged by the present application is that the linker are provided to a particle prior to an assay that is prior capture of a target molecule. FIG. 10 shows particles that are pre-loaded with binding molecules attached to the surface via a long and rigid linker molecule as defined herein above.

Figure 11:
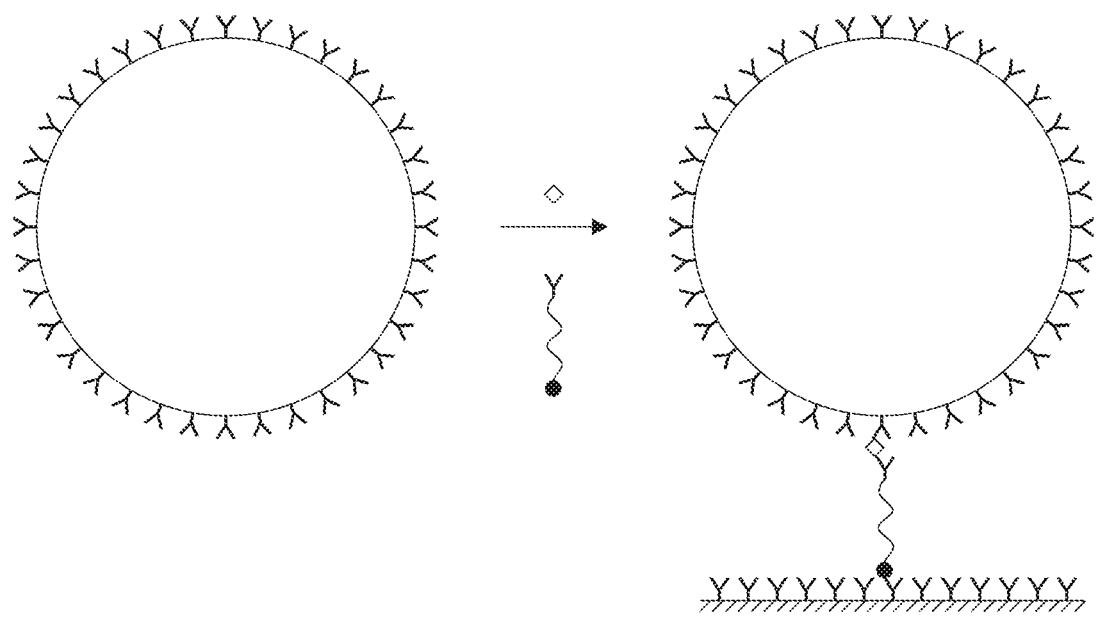
FIG. 11 depicts a particle, pre-loaded with capture molecules attached directly to the surface. During the assay, the target molecule (diamond) is bound to the particle and a second capture molecule recognizing the target, which is connected to a long, rigid linker. The other end of the linker is connected to a recognition element (e.g. biotin), which can bind to a compatible capture molecule (e.g. streptavidin) on the sensor surface.

In particularly preferred embodiments of the present invention, the surface structure of the flat sensor surface is formed after the second binding molecule which is attached to a long linker has recognized the target molecule having bound the first binding molecule. As illustrated in FIG. 11, the second binding molecule is attached to a linker molecule. The other end of the linker molecule comprises a molecule for anchoring of the linker molecule to the surface. An exemplary molecule for this purpose is, for instance, biotin that is able to bind to streptavidin on the flat sensor surface. The envisaged effect of this approach is shown in FIG. 12, where specific binding may only occur by virtue of binding of the second bind molecule with a long linker leading to an increased end-to-end distance of particle and flat sensor surface.

In further preferred embodiments of the present invention the first and/or second particle as defined herein may further comprise a repulsive surface structure. The term "repulsive surface structure" as used herein refers to a structure which may be directly or indirectly attached to the surface of a particle as described herein. A repulsive surface structure within the meaning of the present invention comprises molecules, polymers or and/or a mesh of molecules capable of conferring a repulsive force. The term "repulsive force" as used herein refers to forces, which lead to a repulsion of molecules or particles. Preferably envisaged by the present invention is the repulsion of magnetic particles. In general, a repulsive force between particles may be the result of interparticle forces such as excluded volume repulsion, electrostatic repulsion, entropic forces, or steric forces between polymer covered surfaces. The term "excluded volume repulsion" means the impossibility of any overlap between solid particles or, where applicable, between solid particles including surface structures present on the particles. "Electrostatic repulsion" between particles is observed when particles carry a net electrical charge. If two particles carry the same net charge, i.e. either positive or negative charge they will repel each other. The term "entropic forces" refers to forces which are based on the second law of thermodynamics, describing the tendency of a system to progress to a state in which entropy is maximized. This can result in effective repulsive forces between solid spheres, e.g. magnetic particles. The term "steric repulsive force" is based on a steric effect. It is to be understood that on the atomic level, steric effects arise from the fact that each atom within a molecule occupies a certain amount of space. If atoms are brought to close to each other, the associated cost in energy is high due to overlapping electron clouds (Pauli or Born repulsion) and may affect the molecule's preferred shape or conformation and reactivity. Hence, steric hindrance or steric effects can be seen as repulsion between the electron clouds of the individual atoms and can in principal be defined as a result of electrostatic repulsion on the atomic level.

The wording "wherein said repulsive surface structure conveys a pushing effect on said particles towards said sensor surface" as used herein means that an entire ensemble of particles is pushed towards the sensor surface. This overall pushing effect is based on or caused by electrostatic pushing effects of repulsive surface structures of a particle, e.g. a electrostatic pushing effect between two or more particles, or steric pushing effects of repulsive surface structures of a particle, e.g. a steric pushing effect between two or more particles, or a combination of both, an electrostatic pushing effect and a steric pushing effect of a particle, e.g. between two or more particles. The overall pushing effect may, for example, be dependent on the number of particles in the assay, the number of particle in the vicinity of the sensor surface, the overall charge of two or more particles, the proportion of electrostatic vs. steric pushing, and further parameter known to the person skilled in the art. These parameters may be adjusted and/or modified in accordance with specific needs and necessities of embodiments of the device or of assays carried out as described herein.

In a further preferred embodiment of the present invention the overall pushing effect as defined herein above is determined by measuring the increase of the surface interaction. The term "increase of the surface interaction" as used herein refers to an increase of the amount or number of particles being present at or close to the sensor surface as a result of the repulsion forces between particles, e.g. magnetic particles, according to the present invention. In other words, the increase of surface interaction thus means the increase of interaction of particles with the sensor surface. The increase of surface interaction can be measured via the amount of time the particles spend in close contact with the sensor surface. The term "close contact" means that the particles are near or at the surface so as to generate a signal when being close enough to the sensor surface, e.g. a light signal, using appropriate measurement methods. Suitable methods for the measurement of particles near or at the sensor surface are known in the skilled person and have been described, e.g. in Bruls et al., Lab Chip, 2009, 9. 2504-3510.

In preferred embodiments of the present invention the increase in surface interaction is determined by measuring the signal amplitude during the assay. Without being limited thereto, one envisaged example of determining the increase of surface interaction is the measurement of the signal amplitude via frustrated total internal reflection (FTIR) as described herein. The resulting FTIR signal amplitude then corresponds to the number of particles present in the evanescent field.

The increase of surface interaction is calculated from the signal amplitude resulting from the measurement using particles, e.g. magnetic particles, functionalized with a repulsive surface structure as defined herein above in relation to the signal amplitude resulting from the measurement using non-functionalized particles, e.g. magnetic particles, i.e. particles without any repulsive surface structure. For instance, if the increase of the surface contact is increased by a factor of two, i.e. the signal amplitude using magnetic particles functionalized with a repulsive surface structure is double the signal amplitude of non-functionalized particles, e.g. magnetic particles, the increase in the surface interaction is 100%.

In preferred embodiments of the present invention the increase of the surface interaction between particles and the sensor surface, may be at least about 1%. The increase of the surface interaction may, for example, be 1%, 2%, 3%, 4%, 5%, 6%, 7%, 8%, 9%, 10%, 15%, 20%, 25%, 30%, 35%, 40%, 45%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, 500% or more than 500%.

In particularly preferred embodiments of the present invention a repulsive surface structure may be a charged structure or a steric coating present on the particle, e.g. magnetic particle.

A "steric coating" as used herein refers to a surface structure, which may be present on a particle in the form of a coating, and which provides repulsion between particles. One important effect envisaged by the present invention is that the presence of such a steric coating will result in an increased mutual repulsion of the particles which repulsion in turn leads to the formation of a pushing force thus resulting in a pushing of the particles toward the flat sensor without the need to increase the particle concentration as described in the art (pushing effect). The envisaged approach has thus the effect that the surface contact of the particles increases with the repulsion force of the particles thus leading to an increased reaction rate and finally to increased signal changes at the end of the assay.

The present invention describes one way of how this effect can be achieved, namely by providing a mesh of molecules on the particles surface which may act as a steric coating or barrier to prevent unspecific binding of unrelated molecules, or, which keeps other molecules or particles in a certain distance. It will be appreciated by the skilled person that particles having such a steric coating, e.g. in form of a coating comprising a mesh of molecules, may exert a certain steric repulsion.

The coating on the particles may be such that they form a network or mesh of molecules. Therefore, a layer of a coating according to the present invention may be comprised of small units or entities, which have identical or similar chemical, physical and/or biological properties. Preferably, a layer of the coating as described herein may comprise biological or chemical molecules capable of forming polymers of a certain length. Suitable polymers are, for instance, carbohydrates, lipids, polyethylene glycol, polysaccharides, dendrimers, dendrons, nanotubes, or a mixture thereof. Preferably, these polymeric entities are comprised in linker- or spacer molecules. In specific embodiments of the present invention, the coating may be comprised of a single surface layer or a multilayer shell structure.

The term "spacer molecules" as used herein refers to molecules, which primarily have the function of a spacer. For this purpose, these polymeric molecules have a certain length and strength in order to be able to act like polymeric fibers.

In specific embodiments of the present invention, the spacer molecules may have a length of up to about 500 nm, e.g. up to about 450, 400, 350, 300, 250 nm, 200, 150, 100, 90, 80, 70, 60, 50, 40, 30, 20, or 10 nm.

In further specific embodiments of the present invention, the spacer molecules may be linear, circular, or branched-like molecules, or a mixture thereof. If they are branched, they may be branched in different degrees, e.g. show 2, 3, 4, 4 or more hierarchical levels. The present invention further envisages a combination of different types, e.g. linear and branched, different branching degrees, different spacer lengths etc. of spacer molecules within a network, layer or shell structure. In alternative embodiments of the present invention the spacer molecule or mixture of spacer molecules provide an uniform mesh or network, i.e. an equispaced mesh or network with openings of essentially the same size. It is also envisaged that the mesh be provided with openings. It is in particular preferable if the mesh is so uniform, so that functional properties of the mesh with respect to the approachability of molecules and the motional freedom of molecules are uniform. These parameters may be adjusted by the lengths, branching degree etc. of the spacer molecules.

In further preferred embodiments the linker molecule is longer than the surface structure. The term "longer" as used herein means that the average extension length of the linker molecule is larger than the average extension length of the surface structure. The difference in average extension length may be 5%, 10%, 15%, 20%, 30%, 50%, 75%, 100%, 200%, 300%, 500%, 1000% or more.

In further specific embodiments of the present invention, the spacer molecules can directly or indirectly be interlinked so as to form a three dimensional mesh of molecules. Such an interlinking may be based on functional groups at the termini of a molecule, or located in the center of a molecule, e.g. in case branching is envisaged. The control of interlinkage, its degree etc. may be implemented according to principles and methods known to the person skilled in the art, e.g. from a qualified textbook such as "Bioconjugate techniques", Hermanson, $2^{nd}$ Ed. Academic Press, Elsevier or "Dendrimers and other dendritic polymers" Frechet and Tomalia, J. Wiley.

Suitable spacer molecules within the context of the present invention may be, for example, carbohydrates, lipids, polyethylene glycol (PEG), polysaccharides, dendrimers, dendrons, or nanotubes as defined herein, or any suitable derivatives or combinations thereof. The group of spacer molecules may further comprise hydrocarbon-based surfactants, cholesterol, glycolipids, bile acids, saponins, fatty acids, synthetic amphipathic block copolymers, natural products like egg yolk phospholipids.

A preferred example of a spacer molecule suitable for steric coatings is a polyethylene glycol (PEG) molecule. Polyethylene glycol molecules are capable of forming a dense and voluminous mesh of molecules on a surface. It will be also appreciated by the skilled person that PEG molecules can be interlinked to form a suitable steric coating as described herein above. Suitable molecules for interlinking of PEG molecules are connector molecules as described herein. The length may be made dependent on the envisaged overall thickness of the resulting coating layer, the envisaged length of the linker molecule, the envisaged flexibility, rigidity or stability of the linker molecule, and/or the envisaged number of structure molecules per particle.

Also envisaged by the present invention is the number of polyethylene glycol molecules attached on the particle. It is understood that the more molecules be attached to the particle the higher the density and thickness of the coating layer leading to a particle-particle repulsion through steric effect. It is thus understood that the steric repulsion of the particle is dependent of the thickness of the coating layer, which depends on the number of PEG molecules on the magnetic particles, the length of the PEG molecule and the number of bondages between the PEG molecules. The number of the molecules per particle may be at least about 10, 20, 30, 40, 50, 60, 70, 80, or 90, more preferably at least about 100, 150, 200, 250, even more preferably at least about 300, 350, 400, or 450, and most preferably at least about 500, or 1000.

In further embodiments of the present invention, the number of polyethylene glycol molecules as defined herein above attached to the particle may be varied. In specific embodiments, the number of the polyethylene glycol molecules per particle may be set to about 10, 20, 30, 40, 50, 60, 70, 80, or 90, more preferably to about 100, 150, 200, 250, even more preferably to about 300, 350, 400, or 450, and most preferably to about 500, 550, 600, 650, 700, 750, 800, 850, 900, 950, or 1000. In further embodiments, the number of the polyethylene glycol molecules per particle may be set to about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, 100000, 110000, 120000, 150000, or more. The number of polyethylene glycol molecules per particle may further be made dependent on the size or diameter of the particle, the area in which an attachment is possible or suitable, the ratio between the size or diameter of the particle and the length of the particle, the molecular identity of the polyethylene glycol molecules or any other suitable parameter known to the person skilled in the art.

In further embodiments, the surface coverage of a particle by polyethylene glycol molecules may be at about 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the overall surface of the particle or any value in between theses values.

In further embodiments a steric coating as defined herein conveys a hydrodynamic radius of a particle according to the present invention of at least about 105% of the radius of a particle as defined herein. The term "hydrodynamic radius of a particle" as used herein refers to the effective radius of a hydrated particle comprising a steric coating in solution, or the apparent size of the particle comprising a steric coating in solution. Preferably, a steric coating refers to a multitude, e.g. all, of the molecules contributing to the steric effect as described herein. The hydrodynamic radius of a particle comprising a steric coating as defined herein may be at least about 105% of the radius of a particle as defined herein, in particular of the radius of a particle which does not comprise such a steric coating. The hydrodynamic radius of a particle comprising a steric coating as defined herein may be, for example, about 105%, 110%, 120%, 125%, 130%, 140%, 150%, 160%, 170%, 180%, 190%, 200%, 250% or any value in between these values or more of the radius of a particle as defined herein, e.g. a magnetic particle, in particular of a particle which does not comprise such a steric coating.

In other particularly preferred embodiments of the present invention, the particles may comprise a charged structure in order to generate a repulsion force between the particles. The term "charged structure" as used herein refers to an entity, which contributes to the net charge of a particle according to the present invention. Charged structures according to the present invention may have a net charge that can be either positive or negative. It is understood that a charged structure is not limited to a specific type or form of molecules. A charged structure may, for example, comprise a polymer of one type of molecules or of two or more different types of molecules, a complex of different molecules or entities, or a compound comprising several molecules having different charges, e.g. different positive charges, different negative charges, or (different) positive and negative charges, resulting in a positive or negative overall net charge. Tools and methods for charge calculation are known to the skilled person, e.g. from Dewar, M. J. S., The Molecular Orbital Theory of Organic Chemistry, McGraw-Hill, and Inc., 1969; or Stewart, R., The Proton: Applications to Organic Chemistry, Academic Press, Inc., 1985, 72.

In specific embodiments of the present invention, the charged structure may be attached to the particle directly or indirectly so as to result in a specific net charge of the particle. The specific net charge can be either positive or negative. It is also conceivable that different charged structures are attached on the same particle to result in a mixture of charged structures. Within the context of the present invention a charged structure may cover the surface of the particle so as to provide an overall charged molecule having a specific net charge. It is known to the skilled person that the net charge of a nanoparticle can be determined, for example, via the measurement of the zeta-potential.

One envisaged advantage is that the increased repulsion due to the presence of increased charges on the particle, preferably magnetic particle, leads to increased electrostatic repulsion, which in turn minimizes non-specific clustering of the particles. Reduction of non-specific clustering may help to reduce the background level without the use of a surfactant thus leading to improvement of the blank level in optomagnetic detection assays as described herein and thus improves the limit of detection. Another important effect envisaged by the present invention is that the presence of an increased charge on the particles, being either a negative or a positive charge, will result in an increased mutual electrostatic repulsion of the particles which in turn leads to the formation of an electrostatic "pushing" force thus resulting in a pushing of the particles toward the flat sensor without the need to increase the particle concentration as described in the art. The envisaged approach has the effect that the surface contact of the particles may increase with the charge of the particles, thus leading to an increased reaction rate and finally to increased signal changes at the end of the assay.

In further preferred embodiments, the increased presence of a charge on the particles can be achieved either by providing a linker molecule as described herein comprising or consisting of a charged structure or by providing a charged structure attached to the particles in addition to a linker molecule.

In specific embodiments of the present invention charged structures may cover the entire surface of a particle so to as to provide an overall charged molecule having a specific net charge. In alternative embodiments, charged structures may cover only portions, areas or sectors of a particle, e.g. 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or less of the overall surface of a particle, or any value in between theses values.

In further embodiments of the present invention, the number of charged structure molecules attached to the particle may be varied, e.g. in accordance with an envisaged overall net charge of the particle. It is understood that the overall net charge of the particle varies, e.g. increases or decreases with the number of charged molecules being attached to the particle. The zeta potential (mV) may accordingly increase (negatively) with increasing amount of particles as well as with increasing length of the molecules. It is thus conceivable that the sum of charges present on a particle contributes to the overall net charge. It is further appreciated that the overall net charge of the particle is a function of, inter alia, the number of molecules present on the magnetic particle and the length of the molecule, their positive or negative charge etc. In specific embodiments, the number of the charged structure molecules per particle may be set to about 10, 20, 30, 40, 50, 60, 70, 80, or 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, 100000, 110000, 120000, 150000, or more. The number of the charged structure molecules per particle may be different or be made dependent on the size or diameter of the particle, the area in which an attachment is possible or suitable, the ratio between the size or diameter of the particle and the length of the particle, the molecular or chemical identity of the charged structure molecules, the envisaged use, e.g. assay, or any other suitable parameter known to the person skilled in the art.

Suitable charged structures in order to obtain this electrostatic pushing effect as described herein may comprise a biological or chemical structure or compound capable of contributing to a specific net charge such as a nucleic acid, a ribonucleic acid, a peptide, a polypeptide or protein, a carbohydrate, a lipid, or a polysaccharide, or any suitable derivatives or combinations thereof. Also envisaged are a hydro-gel, and a polymeric charged structures. Preferred is the use of nucleic acid based charged structure molecules.

"Nucleic acid based charged structure molecules" may be any nucleic acid molecules, or derivate or analog thereof. Such charged structure molecules may, for example, comprise single and/or double stranded DNA or RNA molecules, or any type of derivative thereof. Such charged structure molecules may further comprise, or consist of a PNA, CNA, HNA, LNA or ANA molecule as defined herein above, or any mixture or combination thereof, e.g. a combination of any one of DNA, RNA, PNA, CNA, HNA, LNA and ANA or a mixture of LNA nucleotides with DNA or RNA bases, or any mixture or combination with any other charged structure molecule as defined herein. In the context of nucleic acid based charged structures nucleic acids or analogs thereof may additionally be provided with chemical groups or units which carry a charge. For example, phosphate groups, charged nitrogen derivatives or charged sulfur derivatives may be included or added. Furthermore, charges may be accumulated by providing duplex molecules of which at least one molecule comprises charges, e.g. a duplex comprising DNA.

In particularly preferred embodiments of the present invention, the particles, e.g. magnetic particles, may be functionalized with charged structures, e.g. single stranded or double stranded nucleic acid, in particular dsDNA, which may have a varying length. The charge on the particles may accordingly be measured by virtue of their zeta potential. Envisaged by the present invention is that the surface contact of the particles increases with the charge of the particles thus leading to an increased reaction rate and finally to increased signal changes at the end of the assay. In certain embodiments of the present invention, a charged structure such as a nucleic acid may be present in a double-stranded or duplex form, i.e. comprising a strand and a complementary or anti-parallel counter-strand of a nucleic acid molecule associated by base pairing between the strands, or a sense or antisense-strand of a nucleic acid molecule. Alternatively, the charged structure may comprise a single-stranded nucleic acid or a single stranded ribonucleic acid molecule.

In a particular preferred embodiment of the present invention the charged structure comprises a molecule selected from the group consisting of a double stranded or dsDNA, double stranded or dsRNA, PNA, a PNA-DNA duplex, and a RNA-DNA duplex. One advantageous aspect, which is also envisaged by further preferred embodiments of the present invention, is that PNAs and PNA/DNA or PNA/DNA duplexes are not easily recognized by either nuclease or proteases making them resistant to enzymatic degradation.

In further embodiments of the present invention suitable nucleic acid based charged structure molecules may also comprise or consist of single stranded DNA molecules of different base compositions and/or lengths. The single stranded molecules may, for example, encompass the repetition of base sequence, be entirely random, or be derived from nature, or be of only one base.

The nucleic acid based charged structure molecules or combinations thereof as defined herein above may be of different base compositions and/or lengths. The length of the molecule may vary between about 5 nucleotides to about 5000 nucleotides, preferably between about 50 nucleotides to about 3000 nucleotides, between about 100 nucleotides to about 2000 nucleotides even more preferably, most preferably between about 400 nucleotides to about 1000 nucleotides. Also envisaged are other lengths or any length value within the indicated range. The molecule may, for example, have a length of about 10, 20, 30, 40, 50, 60, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000 nucleotides or more, or any number of nucleotides in between the mentioned values.

The length of the nucleic acid based charged structure molecules may be made dependent on the envisaged overall specific net charge, the envisaged length of the linker molecule, the envisaged flexibility, rigidity or stability of the linker molecule, and/or the envisaged number of charged structure molecules per particle. Suitable methods for the calculation of net charges would be known to the person skilled in the art, or can be derived from suitable literature sources.

In further embodiments of the present invention, the number of nucleic acid based charged structure molecules as defined herein above attached to the particle may be varied, e.g. in accordance with an envisaged overall net charge of the particle. It is understood that the overall net charge of the particle varies, e.g. increases or decreases with the number of nucleic acid based charged structure molecules being attached to the particle. In specific embodiments, the number of the nucleic acid based charged structure molecules per particle may be set to about 10, 20, 30, 40, 50, 60, 70, 80, or 90, more preferably to about 100, 150, 200, 250, even more preferably to about 300, 350, 400, or 450, and most preferably to about 500, 550, 600, 650, 700, 750, 800, 850, 900, 950, or 1000. In further embodiments, number of the nucleic acid based charged structure molecules per particle may be set to about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, 100000, 110000, 120000, or 150000. The number of nucleic acid based charged structure molecules per particle may further be made dependent on the size or diameter of the particle, the area in which an attachment is possible or suitable, the ratio between the size or diameter of the particle and the length of the particle, the molecular identity of the nucleic acid based charged structure molecules or any other suitable parameter known to the person skilled in the art. In further embodiments, the surface coverage of a particle by nucleic acid based charged structure molecules may be at about 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the overall surface of the particle or any value in between theses values.

Peptide molecules, polypeptide molecules or protein molecules, e.g. as defined herein above, may also be or comprise suitable charged structures due to the presence of charged entities within the amino acids. It is described in the art that the amine and carboxylic acid functional groups found in amino acids allow them to have amphiprotic properties. Carboxylic acid groups ($-CO_2H$) can be deprotonated to become negative carboxylates ($-CO_2-$), and alpha-amino groups ($NH_2-$) can be protonated to become positive alpha-ammonium groups ($NH_3-$). The skilled person also knows that at pH values greater than the pKa of the carboxylic acid group the negative carboxylate ion predominates. At pH values lower than the pKa of the alpha-ammonium group the nitrogen is predominantly protonated as a positively charged alpha-ammonium group. The skilled person is further aware of the fact that the net charge of an amino acid depends on the pH and the pKa value. Tools and methods to calculate the net charge of an amino acids, peptides, polypeptides or proteins would be known to the person skilled in the art or can be derived from qualified literature references such as the Compute pI/Mw tool which allows the computation of the theoretical pI (isoelectric point) and Mw (molecular weight) for a list of UniProt Knowledgebase (Swiss-Prot or TrEMBL) entries or for user entered sequences (Gasteiger E., et al.; Protein Identification and Analysis Tools on the ExPASy Server; (In) John M. Walker (ed): The Proteomics Protocols Handbook, Humana Press (2005). Such peptide, polypeptide or protein charged structures may be of different amino acid compositions and/or lengths. The length may be made dependent on the envisaged overall specific net charge, the envisaged length of the linker molecule, the envisaged flexibility, rigidity or stability of the linker molecule, and/or the envisaged number of charged structure molecules per particle. It is understood that the overall net charge of the particle is a function of the number of protein or peptide molecules on the particle, e.g. magnetic particle and the length of the molecule.

In further embodiments of the present invention, the number of charged peptide, polypeptide or protein molecules as defined herein above attached to the particle may be varied, e.g. in accordance with an envisaged overall net charge of the particle. In specific embodiments, the number of the charged peptide, polypeptide or protein molecules per particle may be set to about 10, 20, 30, 40, 50, 60, 70, 80, or 90, more preferably to about 100, 150, 200, 250, even more preferably to about 300, 350, 400, or 450, and most preferably to about 500, 550, 600, 650, 700, 750, 800, 850, 900, 950, or 1000. In further embodiments, the number of the charged peptide, polypeptide or protein molecules per particle may be set to about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, 100000, 110000, 120000, 150000, or more. The number of charged peptide, polypeptide or protein molecules per particle may further be made dependent on the size or diameter of the particle, the area in which an attachment is possible or suitable, the ratio between the size or diameter of the particle and the length of the particle, the molecular identity of the charged polypeptide or protein molecules or any other suitable parameter known to the person skilled in the art. In further embodiments, the surface coverage of a particle by charged peptide, polypeptide or protein molecules may be at about 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the overall surface of the particle or any value in between theses values.

A charged structure may, in further embodiments, also be or comprise a carbohydrate molecule, e.g. as defined herein above, which comprises a charged entity capable of contributing to an overall net charge on the particle. Such carbohydrates may be of different compositions and/or lengths. The length may be made dependent on the envisaged overall specific net charge, the envisaged length of the linker molecule, the envisaged flexibility, rigidity or stability of the linker molecule, and/or the envisaged number of charged structure molecules per particle.

In further embodiments of the present invention, the number of charged carbohydrate molecules as defined herein above attached to the particle may be varied, e.g. in accordance with an envisaged overall net charge of the particle. In specific embodiments, the number of the charged carbohydrate molecules per particle may be set to about 10, 20, 30, 40, 50, 60, 70, 80, or 90, more preferably to about 100, 150, 200, 250, even more preferably to about 300, 350, 400, or 450, and most preferably to about 500, 550, 600, 650, 700, 750, 800, 850, 900, 950, or 1000. In further embodiments, the number of the charged carbohydrate molecules per particle may be set to about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, 100000, 110000, 120000, 150000, or more. The number of charged carbohydrate molecules per particle may further be made dependent on the size or diameter of the particle, the area in which an attachment is possible or suitable, the ratio between the size or diameter of the particle and the length of the particle, the molecular identity of the charged carbohydrate molecules or any other suitable parameter known to the person skilled in the art. In further embodiments, the surface coverage of a particle by charged carbohydrate molecules may be at about 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the overall surface of the particle or any value in between theses values A suitable charged structure may further be any lipid molecule, e.g. as defined herein above, which comprises a charged entity capable of contributing to an overall net charge on the particle. The charge in lipids, especially phospholipids is typically determined by the charge of the headgroup. Preferred examples of suitable headgroups capable of conferring a net charge of the lipid molecule are headgroups selected from the group consisting of phosphatidylcholine (PC), phosphatidylserine (PS), phosphatidylethanolamine (PE) and phophatidyglycerol (PG), or any combination thereof.

Such lipids may be of different compositions and/or lengths. The length may be made dependent on the envisaged overall specific net charge, the envisaged length of the linker molecule, the envisaged flexibility, rigidity or stability of the linker molecule, and/or the envisaged number of charged structure molecules per particle.

In further embodiments of the present invention, the number of charged lipid molecules as defined herein above attached to the particle may be varied, e.g. in accordance with an envisaged overall net charge of the particle. In specific embodiments, the number of the charged lipid molecules per particle may be set to about 10, 20, 30, 40, 50, 60, 70, 80, or 90, more preferably to about 100, 150, 200, 250, even more preferably to about 300, 350, 400, or 450, and most preferably to about 500, 550, 600, 650, 700, 750, 800, 850, 900, 950, or 1000. In further embodiments, the number of the charged lipid molecules per particle may be set to about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, 100000, 110000, 120000, 150000, or more. The number of charged lipid molecules per particle may further be made dependent on the size or diameter of the particle, the area in which an attachment is possible or suitable, the ratio between the size or diameter of the particle and the length of the particle, the molecular identity of the charged lipid molecules or any other suitable parameter known to the person skilled in the art. In further embodiments, the surface coverage of a particle by charged lipid molecules may be at about 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the overall surface of the particle or any value in between theses values.

A "hydrogel" comprising a charged structure refers to three dimensional of a network of polymer chains that are hydrophilic, sometimes found as a colloidal gel in which water is the dispersion medium. Typically, hydrogels are highly absorbent, i.e. they can contain over 99.9% water, natural or synthetic polymers and is able to retain large amounts of water with conservation of the network structure. Hydrogels may also possess a degree of flexibility very similar to natural tissue, due to their significant water content. As a result of the high water content, hydrogels are generally considered as biocompatible materials, which makes them particularly interesting for biomedical and pharmaceutical applications. Common ingredients of hydrogels may comprise, for example, polyvinyl alcohol, sodium polyacrylate, acrylate polymers and acrylate copolymers with an abundance of hydrophilic groups. Also envisaged are natural hydrogel materials such as materials including agarose, methylcellulose, hyaluronan and other naturally derived polymers. It is further preferred that hydrogels additionally comprise, comprise or consist of charged elements such as charged polymers or any other charged molecules or moieties, which may be used as charged coating of the particle surface. A homogenous hydrogel structure may advantageously contribute to an overall net charge of the particle leading to electrostatic repulsion of the particles. In a specific embodiment, the linker molecules and other components of the coating or surface structure may be embedded within an aqueous hydrogel framework system, which may further provide a certain stability of the molecules. The skilled person would know how to select suitable charged polymers in order to obtain a hydrogel with an overall net charge. In addition, means and methods for producing suitable hydrogels and attaching these on the particle surface would be known in the art. The hydrogels as described herein above may also comprise a polymeric charged molecule as described herein.

A charged structure may, in further embodiments, also be a "polymeric charged molecule". The term "polymeric charged molecule" or "charged polymer" as used herein refers to a "polymer or copolymer comprising a plurality of repeating units selected from negatively or positively charged repeating units. Such a polymer or copolymer thus works as apolyelectrolyte. It is understood that the charge may be derived from negatively or positively charged groups within the repeating unit. Particularly preferred is a positively charged group selected from the group consisting of a quaternary ammonium group, a primary amine group, a secondary amine group, a tertiary amine group, a quaternary phosphonium group, a tertiary phosphonium group, an amide group, a heteroaromatic nitrogen group, and a sulfonium group.

The resulting positively charged polymers are also termed cationic polymers. The positive charge of a polymeric charged molecule may advantageously prevent the formation of coiled polymers. This allows them to contribute more to viscosity in their stretched state, because the stretched-out polymer takes up more space.

Preferred negatively charged polymers include, but are not limited to, a sulfate ester group, a carboxylate ester group, a phosphate ester group, a sulfone group, a sulfide group, a disulfide group, an ortho ester group, an anhydride group, and a beta-ketosulfone group, or any combination thereof.

Polyelectrolytes have been utilized in the formation of new types of materials known as polyelectrolyte multilayers (PEMs). These thin films are constructed using a layer-by-layer (LbL) deposition technique. During LbL deposition, a suitable growth substrate (usually charged) is dipped back and forth between dilute baths of positively and negatively charged polyelectrolyte solutions. During each dip a small amount of polyelectrolyte is adsorbed and the surface charge is reversed, allowing the gradual and controlled build-up of electrostatically cross-linked films of polycation-polyanion layers. It will be appreciated that such poylectroylte multilayers are suitable to provide particles of the present invention with an overall positive or negative net charge.

In a particularly preferred embodiment of the present invention the linker molecule as define herein and/or the repulsive surface structure as defined herein is not cleavable by DNase. In further specific embodiments of the present invention the linker molecule as defined herein and/or the repulsive surface structure as defined herein is not cleavable by RNase. In addition or alternatively, the linker molecule as define herein and/or the repulsive surface structure as defined herein may not be cleavable by a restriction enzyme capable of cutting a double stranded nucleic acid molecule. Such a non-cleavability by DNase, RNase, or a restriction enzyme may be achieved by providing linker molecules or repulsive surface structures which do not represent a substrate or recognition motif for a DNase enzyme. Typically, the effect could be achieved by using DNA analogues such as PNA, CNA, HNA, LNA or ANA molecules as defined herein, or by using polymeric molecules such as PEG.

Figure 13:
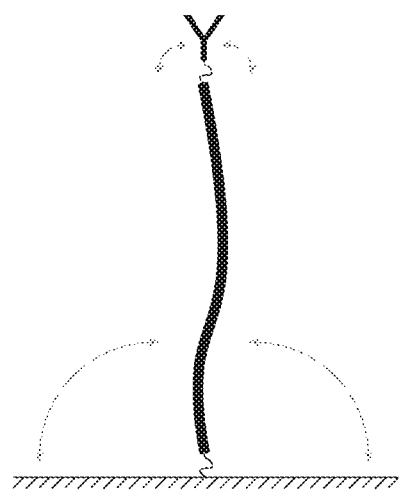
FIG. 13 shows a possible linker design.

In another preferred embodiment of the present invention the linker molecule as defined herein further comprises at least one short flexible spacer. It is accordingly envisaged by the present invention that linker structures as defined herein, preferably long and rigid linkers as define herein, carry at one or a both ends a short flexible spacer. A preferred linker design is shown in FIG. 13. It is appreciated that a certain flexibility due to the presence of such flexible spacer is added to the rigid linker molecule. The flexible spacer structures may thus serve as a flexible joint, which contributes to the mobility of the linker molecule while retaining its overall rigidity. As shown in FIG. 4, the number of possible orientations is increased or facilitated by such a flexible spacer. The flexible spacer may be any suitable flexible molecule, e.g. a polymeric molecule, peptide, chemical group etc.

In a particularly preferred embodiment the short flexible spacer comprises a single stranded nucleic acid, e.g. a single stranded DNA or RNA molecule as defined herein, or any other single stranded nucleic acid form as defined herein or as known to the person skilled in the art.

The present invention in a further aspect relates to a method of detecting the presence or amount of a target molecule within a sample comprising the steps of (a) contacting the sample and a first binding molecule attached to a first particle in a device as described herein above, and (b) contacting the sample with
 i) a second binding molecule capable of attaching to a flat surface or to a second particle, wherein the first binding molecule and/or the second binding molecule are capable of specifically binding to said target molecule, and optionally
 ii) a target analog molecule attached to the flat surface or to the second particle; wherein the target molecule is capable of interfering with the binding of the first binding molecule to the target analog molecule; and (c) detecting the number of first particles bound to the flat surface or to the second particle, wherein the number of particle clusters or of bound particles is directly or inversely related to the amount of target molecules present in the sample.

Envisaged by the present invention are assay formats, which can be either typical competitive or non competitive assays for detection of the presence and/or amount of a target molecule. It will be appreciated by the person skilled in the art that the device as described herein as well as the method according to the present invention are suitable to carry such an analysis.

In the envisaged non-competitive assay format both the first and second binding molecule are capable of specifically binding to the target molecule. It is conceivable that in a first step, the first binding molecule present on a first particle may recognize and bind the target. In a second step the first particle having bound the target molecule may be directed by diffusion or magnetic actuation to a second binding molecule present on a second particle or on a flat sensor surface. Binding to the surface of either the second particle or the flat sensor is mediated by the binding of the second binding molecule to the target. Also envisaged are one or more washing steps, where unspecifically bound particles are removed from the surface. In specific embodiments of the present invention such washing steps occur via pulsed magnetic actuation. The number of bound particles are subsequently detected either by virtue of number of particle clusters or via amount of particles bound to the flat sensor surface as defined herein above. The determined number of bound particles directly corresponds to the number of target molecules within the samples.

Also envisaged are assay formats based on competitive assays, which typically require the presence of a competitor or a target analog. The term "target analog molecule" as used herein refers to any molecule, which competes with the target molecule for the binding to the first binding molecule as defined herein. In such a case the target molecule may interfere with the binding of the first binding molecule to the target analog molecule. Envisaged by the present invention are competition or inhibition assay formats, where the first binding protein may bind a target analog molecule attached on the surface of the flat surface or a particle as defined herein above. This binding can be prevented if a target molecule as described herein is present in the sample and if this target molecule binds to the antibody first. For example, a small drug molecule can be detected using the envisaged method if an analog of the drug molecule is e.g. immobilized to the flat sensor surface. If no drug molecule is present in the sample, all particles with the binding molecule recognizing the target molecule may bind to the target analog molecule on the surface. However, in the presence of drug (target) molecules, which interfere with this binding, the anti-drug binding molecules cannot bind or bind less to the target analog on the surface. In such a case the amount of particles on the surface is inversely related to the amount of target molecules.

Further envisaged by the present invention is the specific use of magnetic particles as defined herein above, which can be actuated by applying a magnetic field such that the analytical procedure can be accelerated. It is also envisaged by the present invention that the use of a magnetic field may be reduce the background signal due to removal of unspecifically bound particles. An exemplary optomagnetic system suitable for the method of detection according to the present invention is illustrated in FIG. 1.

In a further preferred embodiment of the present invention a magnetic force is applied to bring the particles into close proximity with the flat surface or to each other so as to facilitate clustering of the particles.

The term "capable of attaching to the flat surface or second particle" means that the second binding molecule is not necessarily constantly bound to the flat surface or second particle or attached in a predetermined manner, that means is attached to the surface already at the begin of the assay. It is to be understood that the attachment of the second binding molecule to the surface either directly or via a linker molecule as defined herein above may occur at any time point during the assay. It will be appreciated by one of skill in the art that a selective time point of attachment opens up a broad range of possibilities to conduct an assay. Envisaged by the present invention is thus a second binding molecule-linker complex that may act as a separate module independent of its binding to the surface. Such an complex is for instance depicted in FIG. 11. It will be appreciated by the skilled person immediately that a second binding molecule-linker complex that is not constantly fixed or attached at the flat surface may have several advantages. One envisaged advantage is that the unattached second binding molecule-linker complex can diffuse freely and fast, thus enhancing the binding to the capture complex via binding to the target molecule. The term "capture complex" describes a state where the first binding molecule or capture molecule that is directly or indirectly attached to a first particle having captured the target molecule. In this example, the binding of the second binding molecule/linker module to the target molecule that was captured by the first binding molecule may occur timely independent, i.e. occur prior to its attachment to the surface.

In particular preferred embodiments the attachment of said second binding molecule to the flat surface or the second particle occurs prior or after the binding of the second binding molecule to the target molecule. In specific embodiments of the present invention, the second binding molecule is allowed to attach to surface, preferably via a linker molecule as defined herein, in a first step of the assay or prior to the begin of the assay, which is the time point when the sample as defined herein above is added. In such a case, the capture complex is formed first and binds in a subsequent step to a preformed surface structure comprising the second binding molecule attached to the surface.

In further preferred embodiments of the present invention, the second binding molecule-linker module binds to the capture complex by virtue of its specific binding to the target molecule first and the entire capture-second binding molecule-linker complex is subsequently guided to the flat surface or surface of the second particle so as to link the capture complex to the surface. The envisaged idea is illustrated in FIG. 11. In this example, the advantageous distance is generated by a long linker attached to the second antibody, while the first binding molecule is attached to the surface of the first particle directly. In other words, the second binding molecule having attached a long and rigid linker generates the effect leading to enhanced binding kinetics. This specific example demonstrates that the speed of capture complex recognition by the second binding molecule can be maximized due to the module-like attachment as described herein above. Importantly, a major over the art is that the presence of a long and rigid linker as described herein above leads to the distance required for enhancing binding kinetics. The example thus demonstrates that the principle of a long and rigid linker to obtain a enhanced binding kinetics is by no means limited to the linker for attachment of the first binding molecule to the first particle.

It is however also conceivable that both binding molecules are coupled to a long linker in order to further increase or cumulate the advantageous distance between the first particle and the flat surface or the surface of the second binding molecule.

In another preferred embodiment of the present invention the detection of bound particles, e.g. magnetic particles, occurs via frustrated total internal reflection (FTIR) or via measurement of scattered light from said bound particles near the surface or via the optical detection of cluster formation.

Particularly preferred are sensing devices based on an optical detection of particles, especially magnetic particles. Corresponding details may be derived from the exemplary device illustrated in FIG. 1, which comprises a light source and a light detection system, and constitutes a specific embodiment according to the present invention. The optical methods used for detection typically measure the a change in light signal that means a difference in light reflected from the magnetic particles and which can be detected by optical means. For instance, such methods may include techniques such as the detection of scattered light or detection based on total internal reflection (TIR) or frustrated total internal reflection (FTIR). Preferably, the change in light signal refers to only those magnetic particles being bound by virtue of the binding of the second binding molecule to the sensor surface. Details would be known to the person skilled in the art, or can be derived from suitable references, such as Bruls et al., Lab Chip, 2009, 9. 2504-3510.

As used herein the term "total internal reflection" describes a condition present in certain materials when light enters one material from another material with a higher refractive index at an angle of incidence greater than a specific angle. The specific angle at which this occurs depends on the refractive indices of both material, also referred to as critical angle and can be calculated mathematically (Snell's law, law of refraction). In absence of particles, e.g. magnetic particles, no refraction occurs and the light beam from the light source is totally reflected. If a particle, e.g. magnetic particle, is close to the surface or is in contact with the surface the light rays are said to be frustrated by the particle and reflection at that point is no longer total.

The signal, which may be defined as the decrease of the totally internal reflected signal can be calculated. The signal is more or less linearly dependent on the concentration of particles on the surface (surface density ñ). The signal can be expressed as:

$$S=\beta \tilde{n}$$

wherein S is the measured signal change in % and β is a conversion factor from surface density to signal change.

In a preferred embodiment of the present invention detection of bound particles, e.g. magnetic particles, occurs via frustrated total internal reflection (FTIR) or via measurement of scattered light from said bound particles near the surface.

Also envisaged are methods based on the measurement of particle clusters as described in Bruls et al., 2009, Lab Chip, 9, 3504-3510. In another preferred embodiment of the present invention the detection may be carried out via the detection of clusters comprising at least two particles, e.g. magnetic particles and at least one target molecule. For example, a particle, e.g. a magnetic particle, as defined herein above may cluster with further at least one further particle, e.g. magnetic particle, upon the presence of least one target molecule to be detected, which is capable of bridging or combining both particles. In specific embodiments the particle cluster comprises a first and second particle as described herein. The detection may, in a particularly preferred embodiment be carried out in an opto-magnetic system, wherein said particles is are magnetic particles which are magnetically actuated and optically detected in a stationary sample fluid, comprising the steps of (i) target molecule capture, e.g. as defined herein above, (ii) magnetic actuation, and (iii) detection.

In another aspect the present invention relates to the use of a particle as defined herein, e.g. a magnetic particle, for detecting a target molecule within a sample, e.g. a sample as defined herein above.

In a particularly preferred embodiment of the present invention the target molecule as mentioned in the context of the device, method or use as described herein above is cardiac troponin I (cTnI), NT-proBNP or parathyroid hormone. The present invention also aims at the detection of further target molecules or classes or target molecules. Particularly preferred is cardiac troponin I (cTnI).

EXAMPLES

Example 1

Using Long dsDNA as a Linker

The length (extension) of the linker was analyzed in a set of experiments. To this end long dsDNA, which is a very rigid molecule and therefore also results in a far extension from the surface, was used as a linker. In particular, 500 nm streptavidin-coated particles were incubated with dsDNA of varying length. Each DNA molecule contained one biotin moiety at one end of the DNA molecule, a Texas Red molecule at the other end of the molecule. The solution containing particles and DNA were injected into a cartridge and bound to the sensor surface, coated with anti Texas Red antibodies using magnetic attraction. After a magnetic wash step that removed non-bound particles from the surface, the amount of particles that were bound to the surface was determined.

It was found that the kinetics of binding a particle to the surface were significantly enhanced. For instance, for magnetic nanoparticles with an average diameter of ~500 nm, an optimal length of dsDNA of ~700 base pairs (bp), corresponding to a contour length of ~240 nm and an average extension of ~140 nm was observed (see FIG. 6).

A similar experiment was carried out with 1000 nm streptavidin-coated particles As can be seen in FIG. 7, the optimal linker length of 1000 bp (corresponding to a contour length of ~340 nm) is also roughly twice as large. From these measurements, the optimal DNA contour length seems to be roughly ⅔ of the particle radius.

Example 2

Effect of Linker Surface Density on Binding Kinetics

The effect of linker surface density on binding kinetics was tested in an assay format using a 500 nm particle, coated with streptavidin which is bound to a single "target molecule", a dsDNA strand with a biotin on one end and a Texas Red molecule attached to the other end (see FIG. 9, left panel, diamond), that is available to bind to a sensor surface coated with anti-Texas Red antibodies. Subsequently, different amounts of non-functional dsDNA of the same length (but lacking the Texas Red molecule) were bound to the particle as well and the ability of the particles to bind to the sensor surface was compared.

Figure 9:
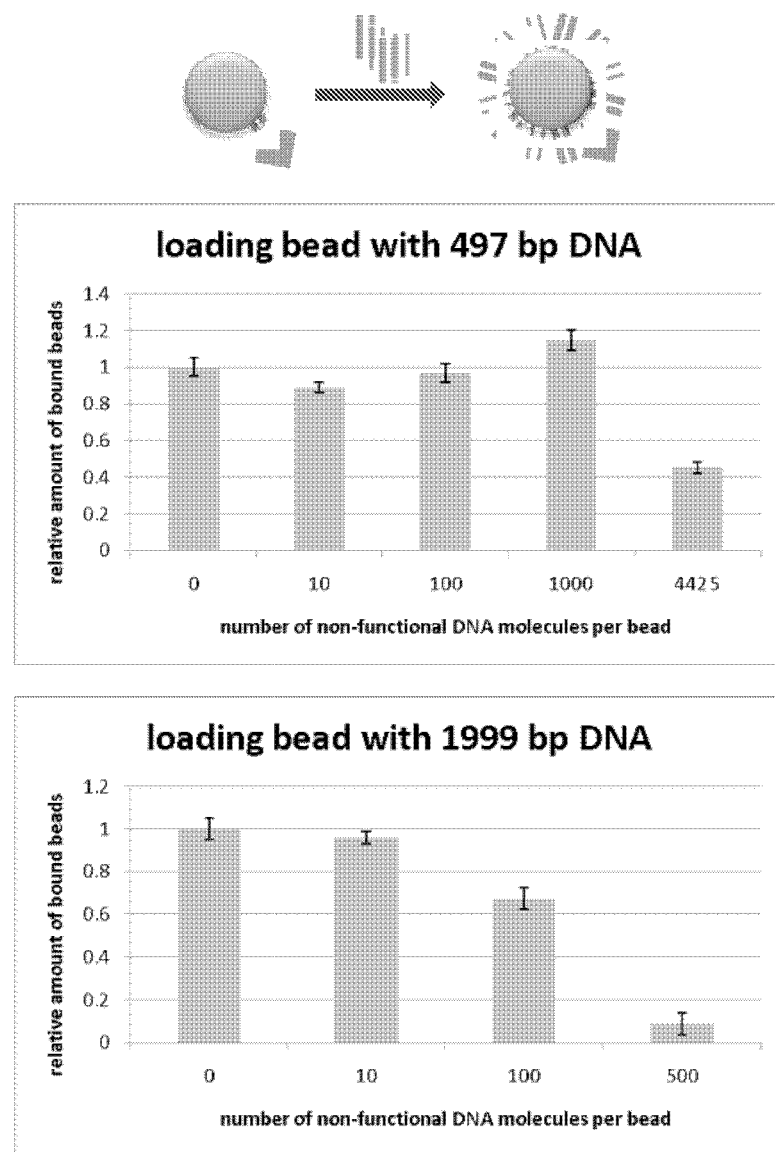
FIG. 9 depicts the effect of linker surface density on binding kinetics. Top: sketch of assay format: a 500 nm particle, coated with streptavidin (orange) is bound to a single target molecule, a dsDNA strand with a biotin on one end and a Texas Red molecule attached to the other end (blue diamond), that is available to bind to a sensor surface coated with anti-Texas Red antibodies. Subsequently, different amounts of non-functional dsDNA of the same length (but lacking the Texas Red molecule) are bound to the particle as well and the ability of the particles to bind to the sensor surface is compared. Middle: particle loading experiment using 1999 bp dsDNA displaying the relative amount of particles binding upon loading with non-functional DNA, as compared to a particle with only 1 functional DNA molecule. Bottom: the same graph, but then for 497 bp DNA.

In a further experiment a particle was loaded with 1999 bp dsDNA. FIG. 9, middle panel, shows the relative amount of particles binding upon loading with non-functional DNA, as compared to a particle with only one "functional" DNA molecule.

In a further experiment a particle was loaded with 497 bp dsDNA. FIG. 9, bottom panel shows the relative amount of particles binding upon loading with non-functional DNA, as compared to a particle with only one "functional" DNA molecule.

The invention claimed is:

1. A system for detecting a target molecule within a sample solution, the device comprising
   (a) a sample container in a biosensor device capable of measuring the target molecule within the sample solution,
   (b) a first particle in the solution, wherein said first particle is functionalized with a first binding molecule capable of specifically binding to said target molecule, and
   (c) a surface structure comprising a second binding molecule capable of binding to the target molecule in the solution, wherein said surface structure covers a flat sensor or is present on a second particle,
   wherein said first particle is capable of binding to said second binding molecule of the surface structure directly or indirectly in the sample container via the target molecule;

wherein (a) the first binding molecule is attached to the first particle via a long and rigid linker molecule, and/or (b) said second binding molecule is attached to a surface of said second particle or the flat sensor surface via a long and rigid linker molecule;

wherein a length and a consistency of each of said long and rigid linker molecules is selected to produce an average extension length defined as the root mean square end-to-end distance of said long and rigid linker molecule in the solution of more than 60 nm and wherein the number of first particles that bind to the flat sensor or are present on the second molecule is directly or inversely related to an amount of target molecules present in the sample solution.

2. The system of claim 1, wherein said first and/or second particle is a magnetic particle.

3. The system of claim 1, wherein the diameter of said first and/or second particle is at least about 100 nm and wherein said average extension length is at least 10% of the diameter.

4. The system of claim 1, wherein the long and rigid linker molecule has an average extension length of at least 20% of a contour length of said long and rigid linker molecule.

5. The system of claim 1, wherein said first binding molecule is an antibody or a fragment thereof, an aptamer, a ligand, or a nucleic acid complementary to the target molecule.

6. The system of claim 1, wherein the first binding molecule is capable of connecting to the first particle by the long and rigid linker molecule, wherein said first particle additionally comprises a repulsive surface structure which is directly attached to the surface of said first particle, wherein said repulsive surface structure covers the surface of the first particle so as to result in a specific net charge and/or a steric repulsion of the first particle, and wherein said repulsive surface structure conveys a pushing effect on said first particles towards said sensor surface, wherein the long and rigid linker molecule is longer than said repulsive surface structure.

7. The system of claim 6, wherein said repulsive surface structure is a charged structure comprising a molecule selected from the group consisting of dsDNA, PNA, a PNA-DNA duplex, and an RNA-DNA duplex.

8. The system of claim 6, wherein said repulsive surface structure is not cleavable by DNase.

9. The system of claim 1, wherein said long and rigid linker molecule further comprises at least one short flexible spacer comprising single stranded nucleic acid.

10. The system of claim 1, wherein said target molecule is cardiac troponin I (cTnI), NT-proBNP or parathyroid hormone.

11. The system of claim 1, wherein the average extension length is $\sqrt{<R^2>}$, where:

$$<R^2>=2Pl[1-(P/l)(1-e^{-l/P})],$$

where, l is a length at maximum physically possible extension of the long and rigid linker molecule, and P is a length of the long and rigid linker molecule over which correlations in the directions of the tangents are lost.

12. The system of claim 1, wherein the long and rigid linker molecule includes a double stranded DNA (dsDNA) of at least 220 base pairs (bp).

13. The system of claim 1, wherein the long and rigid linker molecule includes dsDNA of at least 700 bp.

14. A method of detecting the presence or amount of a target molecule within a sample solution, the method comprising:

(a) contacting the sample solution disposed in a sample container of a biosensor device and a first binding molecule attached to a first particle disposed in the sample container, and (b) contacting the sample solution disposed in the sample container with
  i) a second binding molecule capable of attaching to a flat surface disposed in the sample container or to a second particle disposed in the sample container, wherein the first binding molecule and the second binding molecule are capable of specifically binding to said target molecule,
  ii) a target analog molecule attached to the flat surface or to the second particle, wherein the target molecule is capable of interfering with the binding of the first binding molecule to the target analog molecule; and (c) detecting a number of first particles bound to the flat surface or to the second particle, wherein the number of first particles bound to the flat surface or the second particle is directly or inversely related to an amount of target molecules present in the sample solution;

wherein (I) the first binding molecule is attached to the first particle via a long and rigid linker molecule, and/or (II) said second binding molecule is attached to a surface of said second particle or the flat sensor surface via a long and rigid linker molecule; and wherein a length and a consistency of each of said long and rigid linker molecules is selected to produce an average extension length defined as the root mean square end-to-end distance of said long and rigid linker molecule in the solution of more than 60 nm.

15. The method of claim 14, further including:

applying a magnetic force to the sample solution disposed in the sample container to bring the first particles into close proximity with said flat surface or the second particle so as to facilitate clustering of the particles.

16. The method of claim 14, wherein the attachment of said second binding molecule to the flat surface or the second particle occurs after the binding of the second binding molecule to the target molecule.

17. A system for detecting a target molecule within a sample solution, the system comprising:

a sample container of a biosensor device configured to receive the sample solution including a first particle disposed in the sample container;

first binding molecules in the sample solution configured for specifically binding to said target binding molecule;

a surface structure disposed in the sample container;

second binding molecules configured to bind to the target molecules in the sample solution;

long and rigid linker molecules configured to at least one of:
  connect the first binding molecules to the first particles, or
  connect the second binding molecules to the surface structure, wherein (I) the first binding molecules are attached to the first particles via the long and rigid linker molecules, and/or (II) said second binding molecules are attached to a surface of said second particle or the surface structure disposed in the sample container via the long and rigid linker molecules; and wherein the long and rigid linker molecules have a length and a consistency selected to produce an average extension length defined as the root mean square end-to-end distance of said long and rigid linker molecule in the solution of more than 60 nm.

18. The system of claim 17, wherein the long and rigid linker molecule includes a double stranded DNA (dsDNA) of at least 220 bp.

19. The system of claim 17, wherein the long and rigid linker molecule includes a double stranded DNA (dsDNA) of at least 700 bp.

* * * * *